US008945885B2

(12) United States Patent
Chen et al.

(10) Patent No.: US 8,945,885 B2
(45) Date of Patent: Feb. 3, 2015

(54) MINICIRCLE DNA VECTOR PREPARATIONS AND METHODS OF MAKING AND USING THE SAME

(75) Inventors: Zhi-Ying Chen, Shenzhen (CN); Mark A. Kay, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/567,908

(22) Filed: Aug. 6, 2012

(65) Prior Publication Data
US 2013/0034882 A1  Feb. 7, 2013

Related U.S. Application Data

(63) Continuation-in-part of application No. 12/497,396, filed on Jul. 2, 2009, now Pat. No. 8,236,548.

(60) Provisional application No. 61/155,069, filed on Feb. 24, 2009, provisional application No. 61/078,198, filed on Jul. 3, 2008, provisional application No. 61/562,389, filed on Nov. 21, 2011.

(51) Int. Cl.
| | |
|---|---|
| *C12N 15/64* | (2006.01) |
| *C12N 15/70* | (2006.01) |
| *A61K 48/00* | (2006.01) |
| *C07K 14/195* | (2006.01) |
| *C12N 15/85* | (2006.01) |

(52) U.S. Cl.
CPC .............. *C12N 15/70* (2013.01); *A61K 48/005* (2013.01); *A61K 48/0066* (2013.01); *C07K 14/195* (2013.01); *C12N 15/85* (2013.01); *C12N 2800/108* (2013.01); *C12N 2800/30* (2013.01); *C12N 2800/80* (2013.01); *C12N 2830/002* (2013.01); *C12N 2830/55* (2013.01); *C12N 2800/24* (2013.01)
USPC ...................... 435/91.42; 435/320.1; 435/477; 435/478; 435/488; 536/24.1

(58) Field of Classification Search
None
See application file for complete search history.

(56) References Cited

U.S. PATENT DOCUMENTS

| | | | |
|---|---|---|---|
| 5,922,687 | A | 7/1999 | Mann et al. |
| 5,985,847 | A | 11/1999 | Carson et al. |
| 6,143,530 | A | 11/2000 | Crouzet et al. |
| 6,492,164 | B1 | 12/2002 | Crouzet et al. |
| 2003/0032092 | A1 | 2/2003 | Blanche et al. |
| 2004/0214329 | A1 | 10/2004 | Kay et al. |
| 2006/0223778 | A1 | 10/2006 | Kay et al. |
| 2008/0025958 | A1 | 1/2008 | Hannon et al. |

FOREIGN PATENT DOCUMENTS

| | | |
|---|---|---|
| CA | 2211427 | 8/1996 |
| EP | 0815214 | 7/2007 |

OTHER PUBLICATIONS

Bigger et al., J. Biol. Chem. (2001) vol. 276, No. 25, pp. 23018-23027.*
Acsadi; et al. "Direct gene transfer and expression into rat heart in vivo", New Biol (Jan. 1991), 3(1):71-81.
Chen; et al. "Improved production and purification of minicircle DNA vector free of plasmid bacterial sequences and capable of persistent transgene expression in vivo", Hum Gene Ther (Jan. 2005), 16(1):126-131.
Hickman; et al. "Gene expression following direct injection of DNA into liver", Hum Gene Ther (Dec. 1994), 5 (12):1477-1483.
Khlebnikov; et al. "Homogeneous expression of the P(BAD) promoter in *Escherichia coli* by constitutive expression of the low-affinity high-capacity AraE transporter", Microbiology (Dec. 2001), 147(Pt 12): 3241-3247.
Khlebnikov; et al. "Regulatable arabinose-inducible gene expression system with consistent control in all cells of a culture", J Bacteriol (Dec. 2000), 182(24):7029-7034.
Miao; et al. "Inclusion of the hepatic locus control region, an intron, and untranslated region increases and stabilizes hepatic factor IX gene expression in vivo but not in vitro", Mol Ther (Jun. 2000), 1(6):522-532.
Morgan-Kiss; et al. "Long-term and homogeneous regulation of the *Escherichia coli* araBAD promoter by use of a lactose transporter of relaxed specificity", PNAS (May 2002), 99(11 ):7373-7377.
Wolff; et al. "Direct gene transfer into mouse muscle in vivo", Science (Mar. 1990), 247(4949 Pt 1):1465-1468.
Invitrogen, "One Shot TOP10 Chemically Competent *E. coli*", Invitrogen Corporation (Aug. 2006), 4 pages, retrieved from the Internet: URL: http://pef.aibn.uq.edu.au/support/material/download/One_Shot_TOP10_Competent_Cells.pdf.
Khlebnikov, et al., "Modulation of gene expression from the arabinose-inducible araBAD promoter", Journal of Industrial Microbiology & Biotechnology (Jul. 2002), 29(1):34-37.

* cited by examiner

*Primary Examiner* — Jim Ketter
(74) *Attorney, Agent, or Firm* — Bozicevic, Field & Francis LLP; Kyle A. Gurley; Pamela J. Sherwood

(57) ABSTRACT

The present invention provides minicircle nucleic acid vector formulations for use in administering to a subject, wherein the minicircle nucleic acid vectors include a polynucleotide of interest, a product hybrid sequence of a unidirectional site-specific recombinase, and are devoid of plasmid backbone bacterial DNA sequences. Also provided are methods of producing the subject formulations as well as methods for administering the minicircle nucleic acid vector formulations to a subject. The subject methods and compositions find use in a variety of different applications, including both research and therapeutic applications.

10 Claims, 19 Drawing Sheets

A

| Cp8.araE | ΔendA | araC.3xBAD.IScel | 6xaraC.BAD.ɸC31 | Bla.LacY A177C | Strain D6 |

MINICIRCLE DNA VECTOR PREPARATIONS AND METHODS OF MAKING AND USING THE SAME

GOVERNMENT RIGHTS

This invention was made with government support under federal grant nos. HL 64274 awarded by National Institutes of Health. The United States Government has certain rights in this invention.

BACKGROUND OF THE INVENTION

The introduction of an exogenous nucleic acid sequence (e.g., DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins, as well as therapeutic RNAs, such as interference RNA or ribozymes. Therapeutic applications in which transformation plays a key role include gene therapy applications. Because of the prevalent role transformation plays in the above and other applications, a variety of different transformation protocols have been developed.

In many transformation applications, it is desirable to introduce the exogenous DNA in a manner such that it provides for long-term expression of the protein encoded by the exogenous DNA. Long-term expression of exogenous DNA is primarily achieved through incorporation of the exogenous DNA into a target cell's genome. One means of providing for genome integration is to employ a vector that is capable of homologous recombination. Techniques that rely on homologous recombination can be disadvantageous in that the necessary homologies may not always exist; the recombination events may be slow; etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g., Maloney murine leukemia viral based vectors. Other viral based vectors that find use include adenovirus derived vectors, HSV derived vectors, sindbis derived vectors, etc. While viral vectors provide for a number of advantages, their use is not optimal in many situations. Disadvantages associated with viral based vectors include immunogenicity, viral based complications, as well as integration mediated mutation problems, and the like.

Therefore, there is continued interest in the development of additional methods of transforming cells with exogenous nucleic acids to provide for persistent, long-term expression of an encoded protein. Of particular interest is the development of a non-viral in vivo nucleic acid transfer protocol and vector that provides for persistent protein expression without concomitant genome integration, where the vector provides for persistent expression in a manner that is independent of the sequence and direction of the expression cassette present on the vector.

RELEVANT LITERATURE

U.S. patents of interest include U.S. Pat. Nos. 5,985,847 and 5,922,687. Also of interest are WO/11092 and published U.S. Patent Application Publication No. 20040214329. Additional references of interest include: Wolff et al., "Direct Gene Transfer into Mouse Muscle in Vivo," Science (March 1990) 247: 1465-1468; Hickman et al., "Gene Expression Following Direct Injection of DNA into Liver," Hum. Gen. Ther. (December 1994) 5:1477-1483; Acsadi et al., "Direct Gene Transfer and Expression into Rat Heart in Vivo," New Biol. (January 1991) 3:71-81; and Chen Z Y et al., Human Gene Therapy 16:126, 2005.

SUMMARY OF THE INVENTION

The present invention provides minicircle nucleic acid vector formulations for use in administering to a subject. The minicircle nucleic acid vectors comprise a polynucleotide of interest, e.g. a sequence of interest for expression; a sequence that is the product of a recombination event of a unidirectional site-specific recombinase, and are devoid of plasmid backbone bacterial DNA sequences (plasmid BB). Features of the technology include a minicircle preparation that contains a single population of minicircle comprising a monomer of the transgene expression cassette, which is the optimal structure for delivery and gene expression in vivo and is substantially free of undesirable endonuclease and recombinase genes encoded in circular DNA, allowing making clinical grade of minicircle DNA vector more easily; a procedure that allows the use of greatly reduced amounts of L-arabinose to induce DNA editing enzymes, cutting the minicircle manufacture costs significantly; and a smaller vector size, which allows greater ease of construction for the parental plasmid.

The formulations comprising the minicircle nucleic acid vectors are characterized by being substantially free of contaminating nucleic acid sequences, and more importantly being completely free of circular contaminating nucleic acids sequences coding for a recombinase, such as PhiC31, and/or contaminating nucleic acids sequences coding for a restriction endonuclease, such as ISce 1. Such contaminating sequences are undesirable because, in the unlikely possibility they are transferred into the recipient cells and expressed during the transformation process, the expression product would be capable of damaging recipient's genomic DNA.

Also provided are methods of producing the subject formulations, as well as methods for administering the minicircle nucleic acid vector formulations to a subject. The subject methods and compositions find use in a variety of different applications, including both research and therapeutic applications.

The present invention further provides a system for genomic modification, where an exogenous genetic sequence is integrated into the genome of a targeted cell. Cells targeted for integration include microbial cells, which may be bacterial cells, yeast cells, plant cells and animal cells. Features of the methods include the ability to integrate a contiguous sequence of greater than 10 kb, greater than 15 kb, greater than 20 kb, greater than 25 kb or more. In some embodiments a contiguous sequence of about 10 to about 20 kb is integrated, which may be a sequence of about 12 to about 15 kb. The exogenous sequence is integrated to a targeted site in the genome, allowing for selection of a suitable site, e.g. a site that does not undesirably interrupt sequences of interest.

In the methods of the present invention, one site for the φC31 integrase, which may be an attB or an attP site, is introduced into the targeted site in the genome. Any convenient method may be used for the site directed introduction of the attB or attP sequence. Sequences of interest include the long, native attB or attP recognition sequences, which are up to 300 bp in length. Alternatively an artificial form, e.g. as described in the examples, may be used.

A sequence encoding the φC31 integrase is introduced into the cell, either stably into the genome or as a plasmid. Desirably the integrase is under the control of an inducible promoter.

A circular DNA comprising (a) the desired exogenous sequence to be integrated into the genome, and (b) the complementary site for φC31 integrase (i.e. if attB is present in the genome, then attP is present in the plasmid; if attP is present in the genome then attB is present in the plasmid). Expression of φC31 integrase is induced, and the entire sequence of the plasmid is integrated at the targeted site.

The cell may further include a second recombinase, allowing selective removal of unwanted sequences, such as the hybrid sequences responsible for the reverse recombinase reaction, along with the useless or harmful plasmid backbone DNAs, from the genome. This approach allows removal of one of the two recombination hybrids (either attL or attR), disabling the reverse reaction and resulting in a stable genomic insertion. This type of site-specific integration broadens the ability to make stable genetic modifications in prokaryotic and eukaryotic genomes.

For example, to stabilize the integrant, a double recombination strategy is used. The φC31 integrase is used to mediate an integration event, followed by FLP- or TPin-mediated recombination to remove the attL. This eliminates the possibility of a reverse reaction between the attL and attR. Alternatively the TPin/9attB.9attP recombination system, using the bacteriophage TP901-1 integrase is used to remove the attL or attR sequence.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 9A shows knockout of the wild type LacY gene of the strain CC2øC31 (D2). We used a linear DNA as the targeting sequence, which comprised the tetracycline resistance gene flanked with a 420-bp sequence of LacZ gene and 227-bp of LacA gene up- and down-stream of the LacY gene. We used a same RED-mediated integrating protocol to integrate the linear DNA (FIG. 3A). After selecting the colony with tetracycline marker, we confirmed the LacY gene knockout in the intermediate strain by DNA sequencing of the PCR product generated by the LacZ gene- and tetracycline resistance gene-specific primers (FIG. 9C). Scheme FIG. 9B shows the integration of the mutant LacY A177C (muLacY) at the original place of LacY. Wild type LacY protein is a lactose transporter while muLacY gain additional function as L-arabinose transporter (Morgan-Kiss R M et al., PNAS 99:7373, 2002). The constitutive promoter derived from the beta-lactosidase gene (bla) is used to drive the expression of this mutant To make the integrating DNA, we used the DNA sequence comprising the kanamycin resistance gene flanked with attB and attP and the bla.muLacy cassette to replace the tetracycline gene in the above linear integrating DNA (FIG. 9A). Likewise, we used a same RED-mediated integrating protocol to integrate the mutant LacY (FIG. 3A). We selected the colony with kanamycin resistance marker, followed by removing the kanamycin resistance gene via incubating the bacteria in LB containing 1% Larabinose to induce the øC31-mediated recombination. We confirmed the integrant by DNA sequence of the PCR product generated using the bla- and the LacA-specific primers (FIG. 9D). muLacY, LacY A177C; bla, promoter of the beta-lactosidase gene.

FIG. 10A illustrates the preparation of the target site in the genome of CCD2øC31.muLacy. We succeeded in integrating 2 copies of the BAD.øC31 cassette using the construct p2øC31.R6KFRT (FIG. 8B), but failed to integrate additional copies of øC31 gene by repeating the same procedure. We hypothesized that 3 pre-existed FRT sites block the function of FLP recombinase; the original strain BW27783 carried 2 FRT sites, and the strain CC2øC31 obtained an additional site as a result of integrating 2BAD.øC31. To overcome this problem, we used recombinase phage TP901-1 (TPin), also under the control of araC.BAD system, to replace the FLP. Like øC31, TPin mediates a unidirectional reaction. To distinguish from that of øC31, we used the abbreviates 9attB and 9attP to stand for the bacterial and phage attachment sites of TPin, respectively. With a careful design, the sequential reactions of these two enzymes will generated stable integrants by removing one of two hybrid sequences in each set, i.e., the attL/attR and 9attL/9attR. To target the dispensable araD gene in the genome of the strain CC2øC31.muLacY (FIG. 9B), we used a linear DNA comprising the tetracycline resistance gene, together with the attB and 9attP sites, flanked by a 5'-end 275-bp and a 3'-end 310-bp sequences of the araD gene. After selecting the tetracycline-resistance colony, we confirmed the integrant by DNA sequencing of the PCR product generated using the 5' portion of araD- and polB gene-specific primers; polB gene is downstream of araD in bacterial genome; therefore, we generated the desired intermediate strain CC2øC31.muLacY.ΔaraD (FIG. 10A). Expecting many more copies of øC31 gene are needed, we made another integrating plasmid pA101.4øC31 carrying 4 tandem copies of the BAD.øC31 cassette; we used an alternative temperature sensitive plasmid DNA replication origin A101 which is also curable upon incubating the bacteria at 43° C. (FIG. 10B). To make the strain carrying the additional 4BAD.øC31 cassette, we transformed the strain CC2øC31.muLacY.ΔaraD with the plasmid, and induce the øC31 mediated integration by incubating selected colony in 5-ml LB containing 0.001% L-arabinose at 30° C. for 2 hours. To select the colony with the integrant, we selected the bacterial colonies resistant to both tetracycline and kanamycin. To eliminate the two antibiotic resistant genes, we transformed the bacteria with plasmid pBAD.TPin, and incubated the resulted colony in LB containing 0.001% L-arabinose at 43° C. for 2 hours to induce the TPin-mediated recombination between 9attB and 9attP before spread onto antibiotic-free plate. Subsequently, we incubated the plates at 43° C. overnight; in addition to faster bacteria growth, this step cured the plasmid pBAD.TPin as well Previously, we found that the øC31 was able to mediate a reverse reaction between attL and attR, resulting in the loss of the integrant, probably because the bacteria expressed a cofactor needed for this reverse reaction (data not shown). To minimize this undesired reverse reaction, we incubated the culture at 43° C., for at this temperature, TPin recombinase maintains substantial activity but øC31 has little or no activity (Staphenie M et al., J bacterial 184:3657, 2002). To stabilize the integrant, we designed the targeted sequence and the integrating plasmid in a way that after the sequential recombination reactions mediated by øC31 and TPin, only the hybrids attR and 9attL were left, making the reverse reaction between attL and attR or 9attL and 9attR impossible. To obtain the desired colony, we selected the colonies from the antibiotic-free plate, and confirmed the loss of both antibiotic resistant genes by transferring individual colonies onto the plates containing each antibiotic. We further confirmed the integrant by DNA sequencing of the PCR products, the PR1 and PR2, generated by genome- and integrant-specific primers (FIGS. 10B and 10D). A101, a temperature sensitive plasmid replication origin; None, none specific product; Cont, PCR product from control template DNA.

FIG. 11A-11B. Genotype of the strain D6 and the simplified parental plasmid. FIG. 11A summarizes the genotype of the strain D6. In addition to the Cp8.araE, endA and araC3xBAD.ISce1 gene and 2 copies of the BAD.øC31, the strain D6 carries a second L-arabinose transporter bla.mu-LacY and 4 additional copies of BAD.øC31, with 6 copies BAD.øC31 in total. FIG. 11B, the simplified parental plasmid encoding the RSV.hAAT.bpA cassette.

DEFINITIONS

Figure 1:
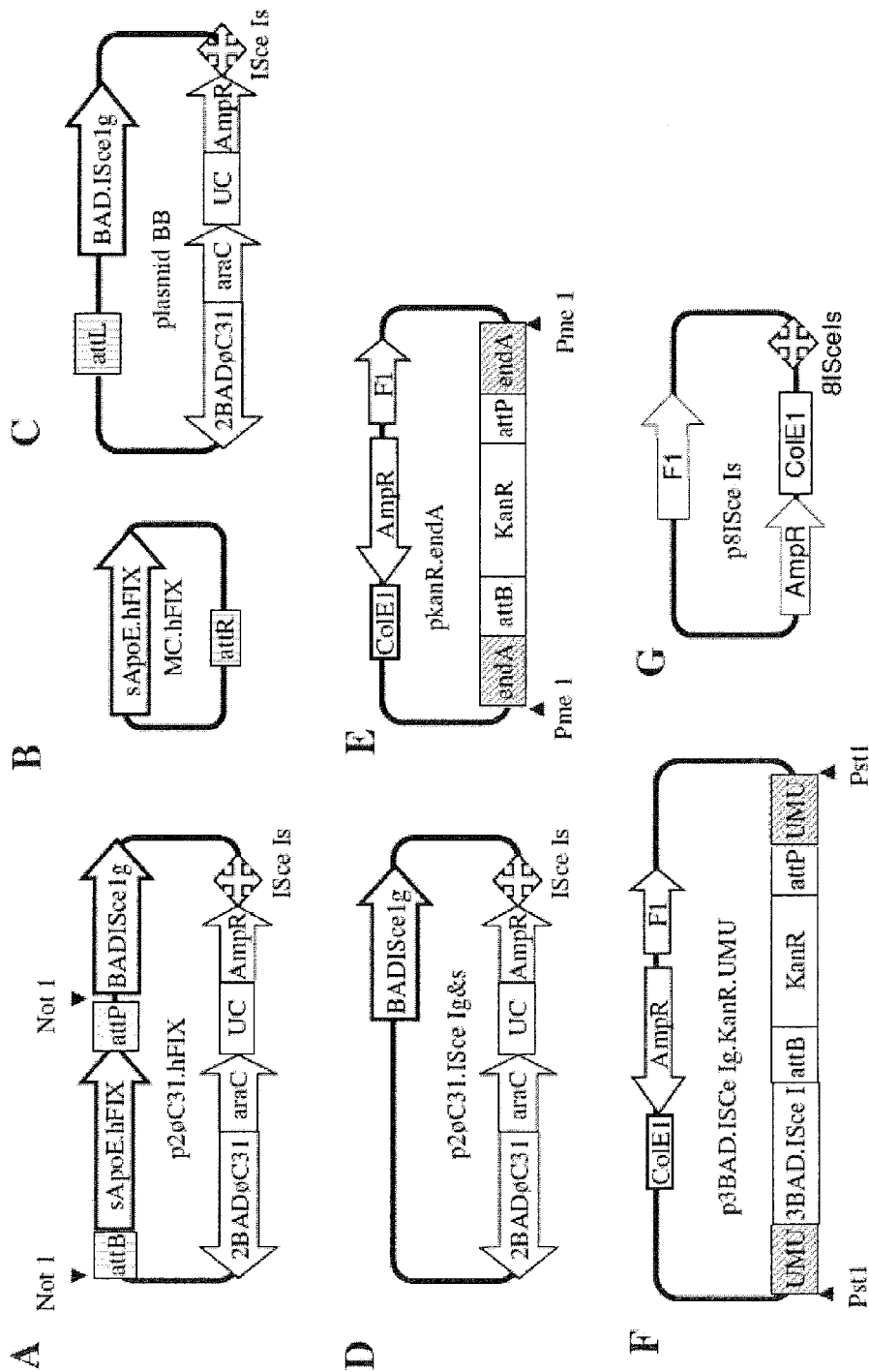
FIGS. 1A-1G show schematics of various plasmids. Panel A shows the p2øC31.hFIX plasmid, the minicircle producing plasmid as described in details previously (Chen et al., Human Gene Therapy 16:126, 2005). BAD, the arabinose-inducible promoter of the araC-BAD regulation system; araC, the repressor gene; øC31, a recombinase gene derived from phage *Streptomyces*; attB, bacterial attachment site of recombinase øC31; attP, the phage attachment site; ISce Ig, the gene encoding the restriction enzyme ISce 1; ISce Is, ISce I restriction site; sApoE, the artificial enhancer/promoter as described in details earlier (Miao et al. Mol Ther 1:522, 2000); hFIX, the gene encoding human coagulation protein factor IX; AmpR, ampicillin resistance gene; UC, plasmid replication origin. Panel B shows the minicircle MC.hFIX encoding the sApoE.hFIX cassette produced from plasmid p2øC31.hFIX via øC31-mediated recombination; MC, minicircle; attR, the right hybrid sequence. Panel C shows the plasmid BB, the plasmid bacterial backbone circle derived from p2øC31.hFIX via øC31-mediated recombination; attL, the left hybrid sequence. Panel D shows the p2øC31.ISce Ig&s plasmid, a plasmid generated by eliminating hFIX cassette and the flanking attB and attP from P2øC31.hFIX of Panel A. Panel E shows the pKanR.endA plasmid, the plasmid for inactivating the bacterial endA gene; KanR, kanamycin resistance gene; endA, the gene encoding the bacterial endonuclease 1. Panel F shows the p3BAD.ISce 1g.KanR.UMU plasmid, the plasmid for integrating 3BAD.ISce I cassette; UMU, bacterial UMU locus. Panel G shows the p8ISce 1s plasmid, a pBlueScript (Stratagene, La Jolla, Calif.) based plasmid carrying 8 consecutive ISce I restriction sites.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors.

An "expression cassette" comprises any nucleic acid construct capable of directing the expression of any RNA transcript including gene/coding sequence of interest as well as non-translated RNAs, such as shRNAs, microRNAs, siRNAs, anti-sense RNAs, and the like. Such cassettes can be constructed into a "vector," "vector construct," "expression vector," or "gene transfer vector," in order to transfer the expression cassette into target cells. Thus, the term includes cloning and expression vehicles, as well as viral vectors.

A "minicircle" vector, as used herein, refers to a small, double stranded circular DNA molecule that provides for persistent, high level expression of a sequence of interest that is present on the vector, which sequence of interest may encode a polypeptide, an shRNA, an anti-sense RNA, an siRNA, and the like in a manner that is at least substantially expression cassette sequence and direction independent. The sequence of interest is operably linked to regulatory sequences present on the mini-circle vector, which regulatory sequences control its expression. Such mini-circle vectors are described, for example in published U.S. Patent Application US20040214329, herein specifically incorporated by reference.

The overall length of the subject minicircle vectors is sufficient to include the desired elements as described below, but not so long as to prevent or substantially inhibit to an unacceptable level the ability of the vector to enter the target cell upon contact with the cell, e.g., via system administration to the host comprising the cell. As such, the minicircle vector is generally at least about 0.3 kb long, often at least about 1.0 kb long, where the vector may be as long as 10 kb or longer, but in certain embodiments do not exceed this length.

Minicircle vectors differ from bacterial plasmid vectors in that they lack an origin of replication, and lack drug selection markers commonly found in bacterial plasmids, e.g. β-lactamase, tet, and the like. Also absent are expression silencing sequences found, for example, in plasmid backbones, e.g. the parental plasmid backbone nucleic acid sequences from which the minicircle vectors are excised. The minicircle may be substantially free of vector sequences other than the recombinase hybrid product sequence, and the sequence of interest, i.e. a transcribed sequence and regulatory sequences required for expression.

By "polynucleotide of interest" or "sequence of interest" it is meant any nucleic acid fragment adapted for introduction into a target cell. Suitable examples of polynucleotides of interest include promoter elements, coding sequences, e.g. therapeutic genes, marker genes, etc., control regions, trait-producing fragments, nucleic acid elements to accomplish gene disruption, as well as nucleic acids that do not encode for a polypeptide, including a polynucleotide that encodes a non-translated RNA, such as a shRNA that may play a role in RNA interference (RNAi) based gene expression control.

The minicircle vectors comprise a product hybrid sequence of a unidirectional site-specific recombinase, which product hybrid sequence is the result of a unidirectional site specific recombinase mediated recombination of two recombinase substrate sequences as they are known in the art, e.g., attB and attP substrate sequences, and may be either the attR or attL product hybrid sequence. Typically, the product hybrid sequence ranges in length from about 10 to about 500 bp. In certain embodiments, the product sequence is a product hybrid sequence of a unidirectional site specific recombinase that is an integrase, where integrases of interest include, but are not limited to: wild-type phage integrases or mutants thereof, where specific representative integrases of interest include, but are not limited to: the integrases of ΦC31, R4, TP901-1, ΦBT1, Bxb1, RV-1, AA118, U153, ΦFC1, and the like.

In the present invention, when a recombinase is "derived from a phage" the recombinase need not be explicitly produced by the phage itself, the phage is simply considered to be the original source of the recombinase and coding sequences thereof. Recombinases can, for example, be produced recombinantly or synthetically, by methods known in the art, or alternatively, recombinases may be purified from phage infected bacterial cultures.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises at least about 50%, such as about 80%-85%; about 90-95%, as well as up to about 99% or more of the desired component. Techniques for purifying polynucleotides and polypeptides of interest are well-known in the art and include, for example, ion-exchange chromatography, affinity chromatography and sedimentation according to density.

The term "exogenous" is defined herein as DNA, such as the DNA constructs defined herein, which is artificially introduced into a cell, e.g. by the methods of the present invention. Exogenous DNA can possess sequences identical to or different from the endogenous DNA present in the cell prior to introduction by transfection, transformation, etc.

Methods of transfecting cells are well known in the art. By "transfected" it is meant an alteration in a cell resulting from the uptake of foreign nucleic acid, usually DNA. Use of the term "transfection" is not intended to limit introduction of the foreign nucleic acid to any particular method. Suitable methods include viral infection/transduction, conjugation, nanoparticle delivery, electroporation, particle gun technology, calcium phosphate precipitation, direct microinjection, and the like. The choice of method is generally dependent on the type of cell being transfected and the circumstances under which the transfection is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "coding sequence" or a sequence that "encodes" a selected polypeptide, is a nucleic acid molecule which is transcribed (in the case of DNA) and translated (in the case of mRNA) into a polypeptide, for example, when the nucleic acid is present in a living cell (in vivo) and placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral, eukaryotic, or prokaryotic DNA, and synthetic DNA sequences. A transcription termination sequence may be located 3' to the coding sequence, and a promoter may be located 5' to the coding sequence; along with additional control sequences if desired, such as enhancers, introns, poly adenylation site, etc. A DNA sequence encoding a polypeptide may be optimized for expression in a selected cell by using the codons preferred by the selected cell to represent the DNA copy of the desired polypeptide coding sequence.

The term "encoded by" refers to a nucleic acid sequence which codes for a polypeptide sequence. In addition, "encoded by" also refers to a nucleic acid sequence which codes for a non-translated RNA, such as a shRNA or antisense RNA, or other small RNA.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Target cell" as used herein refers to a cell that in which a genetic modification is desired. Target cells can be isolated (e.g., in culture) or in a multicellular organism (e.g., in a blastocyst, in a fetus, in a postnatal animal, and the like). Target cells of particular interest in the present application include, but not limited to, cultured mammalian cells, including CHO cells, primary cell cultures such as fibroblasts, endothelial cells, etc., and stem cells, e.g. embryonic stem cells (e.g., cells having an embryonic stem cell phenotype), adult stem cells, pluripotent stem cells, hematopoietic stem cells, mesenchymal stem cells, and the like.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Minicircle DNA Formulations

The present invention provides minicircle nucleic acid vector formulations that are substantially free of contaminating nucleic acids, i.e. non-minicircle nucleic acids, which minicircle nucleic acid vectors provide for persistently high levels of protein expression when introduced into a mammalian target cell. Methods are also provided for producing the minicircle nucleic acid vector formulations. Undesirable contaminating nucleic acids sequences include coding sequences for recombinases, such as PhiC31, and/or contaminating nucleic acids sequences coding for restriction endonucleases, such as ISce 1. Such contaminating sequences are undesirable due to a small possibility of transfer into recipient cells.

These undesirable sequences may be present in the unrecombined parental plasmid and the plasmid backbone circle (plasmid BB), and thus it is desirable to ensure completion of the recombination and restriction digestion. In some embodiments, contamination is reduced by integrating the coding sequences for recombinase and restriction endonuclease into the bacterial chromosome, rather than providing the coding sequences in the parental plasmid.

Minicircle vectors are produced by transfecting a bacterial cell that has been genetically modified to constitutively express araE and to lack functional endonuclease I, with a parental plasmid comprising a sequence of interest flanked by recombination sites for a unidirectional site-specific recombinase, and at least one restriction endonuclease site recognized by a restriction endonuclease not endogenous to the bacterial cell. Present on either the parental plasmid or the bacterial cell chromosome are sequences encoding the unidirectional site-specific recombinase, and the non-endogenous restriction endonuclease that cleaves the parental plasmid. The recombinase and/or the restriction endonuclease coding sequences may be operably linked to an inducible promoter responsive to arabinose. The transfected bacterial cells are grown to the desired concentration, and incubated for a period of time sufficient to activate expression of the unidirectional site-specific recombinase and recombine the attB and attP recombination sites; and to activate expression of the restriction endonuclease and digest the plasmid backbone at the restriction endonuclease site. The incubation step results in the generation of minicircle vectors comprising the polynucleotide of interest and a product hybrid sequence of the unidirectional site-specific recombinase; which lack parental plasmid backbone sequences. The minicircle vectors are then purified to provide a minicircle nucleic acid vector formulation substantially free of contaminating nucleic acids.

In general, the minicircle vector formulations generated by the methods described herein comprise nucleic acids that are at least about 80% minicircle vectors, at least about 90% minicircle vectors, at least about 95% minicircle vectors, at least about 96% minicircle vectors, at least about 97% minicircle vectors, at least about 98% minicircle vectors, at least about 99% minicircle vectors, at least about 99.5 percent minicircle vectors, and at least about 99.9% minicircle vectors. It will be understood by one of skill in the art that the formulation may comprise buffers, excipients and other non-nucleic acid components.

In certain embodiments the purity of the minicircle vector preparation can be quantified by, for example, screening for protein activity that would be present if contaminating nucleic acid coding sequence were present in the preparation. Exemplary such proteins include unidirectional site-specific recombinases and restriction endonucleases not endogenous to the bacterial cells. Therefore, the purity of the minicircle vector preparation can be quantified by screening for the level of activity of the recombinase and/or a restriction endonuclease as compared to a control with a known quantity of such contaminating nucleic acid as well as a negative control lacking in such contaminating nucleic acid. In such embodiments, the minicircle vector preparation will generate at least 1.5 fold less activity than a control preparation, e.g. a control minicircle preparation produced with conventional bacterial cells, or by the methods known in the art, including about 2 fold, 3 fold, 4 fold, 5 fold, 10 fold, 20 fold, 30 fold or less activity than the control. Alternatively, the presence of contaminating recombinase and endonuclease DNA sequences can be detected, e.g. by PCR, etc.

A feature of the subject invention is that the methods and cell lines described herein produce a minicircle vector formulation that is substantially free of contaminating nucleic acid, which contaminating nucleic acid sequences include, without limitation: prokaryotic plasmid backbone sequences; nucleic acid sequences coding for a unidirectional site-specific recombinase, such as PhiC31; and nucleic acid sequences coding for a restriction endonuclease, such as ISce 1. The most prominent feature of the present invention is that the minicircle vectors produced are completely free of circular nucleic acid sequences coding for a unidirectional site-specific recombinase, such as PhiC31; and nucleic acid sequences coding for a restriction endonuclease, such as ISce 1. As they are physically similar to the minicircle vectors, these circular contaminations are more difficult to remove than linear contamination. The site-specific recombinase and restriction enzyme are potentially damaging to target cell genomic DNA. Contaminating nucleic acids include linear nucleic acid fragments and circular nucleic acids.

In general, the minicircle nucleic acid vector formulations of the invention are produced with genetically modified bacteria that provide for efficient expression of one or both of (i) a unidirectional site-specific recombinase and (ii) a restriction endonuclease not endogenous to the bacterial cell. These DNA-modifying components may be encoded by an expression vector and/or genomically integrated expression cassettes, and are expressed in substantially all the bacterial cells during generation of the minicircle vectors from the minicircle parental plasmids, thus ensuring that generation of minicircle vectors and destruction of the parental plasmid backbone proceeds to completion.

As described in greater detail below, in some embodiments the genetically modified bacteria comprise one or more genomically integrated coding sequence(s) for the L-arabinose transporter araE gene under the control of a constitutive promoter, and lack functional endonuclease I expression. In such embodiments, the constitutive expression of the L-arabinose transporter expressed by the cells provides for efficient transport of L-arabinose (when added to the cell culture media) into all the bacteria. As a result of the efficient substrate transport, coding sequences under the control of an inducible promoter responsive to L-arabinose, such as the araC-BAD promoter, efficiently produce the encoded proteins at a consistent, uniform and high level in substantially all the cells in a culture.

The use of such genetically modified bacteria provides multiple advantages in the methods of the invention. (1) It ensures that substantially all the bacteria carrying an extrachromosomal vector and/or genomically integrated expression cassette encoding a unidirectional site-specific recombinase and restriction endonuclease under the control of an inducible promoter, such as araC-BAD, are adequately expressed from limited copies of the genes. (2) It ensures that the recombinase-mediated recombination between the attB and attP and the subsequent formation of minicircle vectors progresses to completion in all cells. As a result, at completion of the process the preparation of minicircle vectors will be substantially free of unrecombined parental plasmids that would otherwise remain due to insufficient expression of the recombinase in at least a subpopulation of the bacteria in the culture. (3) It ensures that in the plasmid backbone DNA destruction phase both the plasmid backbone bacterial DNA circle and the residual unrecombined parental plasmid are cut efficiently in all the bacteria in the culture, which ensures the preparation of minicircle vectors will be in a substantially pure form. (4) Lastly, it allows a lower concentration level of L-arabinose for activating the expression of the recombinase and/or restriction endonuclease gene under the control of an arabinose inducible promoter, thereby providing an additional advantage of a decrease in reagent cost, facilitating a scale up of the methods to provide for production of large quantities of the minicircle vector preparations.

In some embodiments, the genetically modified bacteria comprise: a genomically integrated coding sequence for the restriction endonuclease not endogenous to the bacteria; a genomically integrated coding sequence for the L-arabinose transporter araE gene under the control of a constitutive promoter; and lacking functional endonuclease I expression. In other embodiments, the genetically modified bacteria comprise: a genomically integrated coding sequence for the restriction endonuclease not endogenous to the bacteria and the unidirectional site-specific recombinase; a genomically integrated coding sequence for the L-arabinose transporter araE gene under the control of a constitutive promoter; and lacking functional endonuclease I expression. In such embodiments, by including the coding sequences for the restriction endonuclease and/or the unidirectional site-specific recombinase (collectively referred to as "the enzymes"), the coding sequences for the enzymes is not introduced into the bacteria on a separate circular extrachromosomal expression vector. As a result of genomic integration of the enzyme coding sequences, opportunity for the nucleic acid sequence coding for the restriction endonuclease and/or the unidirectional site-specific recombinase to be present in the minicircle vector preparation as circular contaminating nucleic acids is completely prevented.

It is important to note that when the nucleic acid sequences encoding for the enzymes are genomically integrated, they may still be present during the purification process as a result of shearing of genomic DNA during purification of the minicircle vectors. However, nucleic acid sequences in linear bacterial chromosomal DNA fragments can readily be separated from the minicircle vectors by conventional purification means, as opposed to circular nucleic acids that are more difficult to separate from the minicircle vectors.

By integrating the nucleic acid sequences encoding the unidirectional site-specific recombinase, such as øC31, and/or a restriction endonuclease, such as ISce 1, in addition to the constitutive expression of the L-arabinose transporter, the genetically modified bacteria provide the added advantage of not only ensuring that the process of formation of the minicircle vectors from the parental plasmids proceeds in an efficient manner consistently throughout substantially all the bacteria in the culture, but also the advantage of ensuring that the coding sequences for the enzymes do not contaminate the final minicircle vector preparation. Multiple copies of the nucleic acid sequences encoding the unidirectional site-specific recombinase may be integrated into the genome.

Uses of Genetically Modified Bacterial Cells

In some embodiments, the minicircle vectors are produced in genetically modified bacteria that comprise one or more genomically integrated coding sequence(s) for the L-arabinose transporter araE gene under the control of a constitutive promoter, and which lack functional endonuclease I expression. As noted above, in such embodiments, the constitutive expression of the L-arabinose transporter provides for efficient transport of L-arabinose from the medium to all the cells. Optionally, a second L-arabinose transporter is also constitutively expressed in the bacterial cell. An example of the $2^{nd}$ L-arabinose transporter is the mutant LacY protein; a mutation renders the resulted LacY A177C the L-arabinose-transporting function its wild-type counterpart does not possess (Morgan-Kiss R M et al., PNAS 99:7373, 2002). As a result, the genes under the control of an inducible promoter responsive to L-arabinose, such as the BAD promoter, will efficiently produce the encoded proteins at a consistent, uniform and high level in substantially all the cells in the cell culture.

Figure 6:
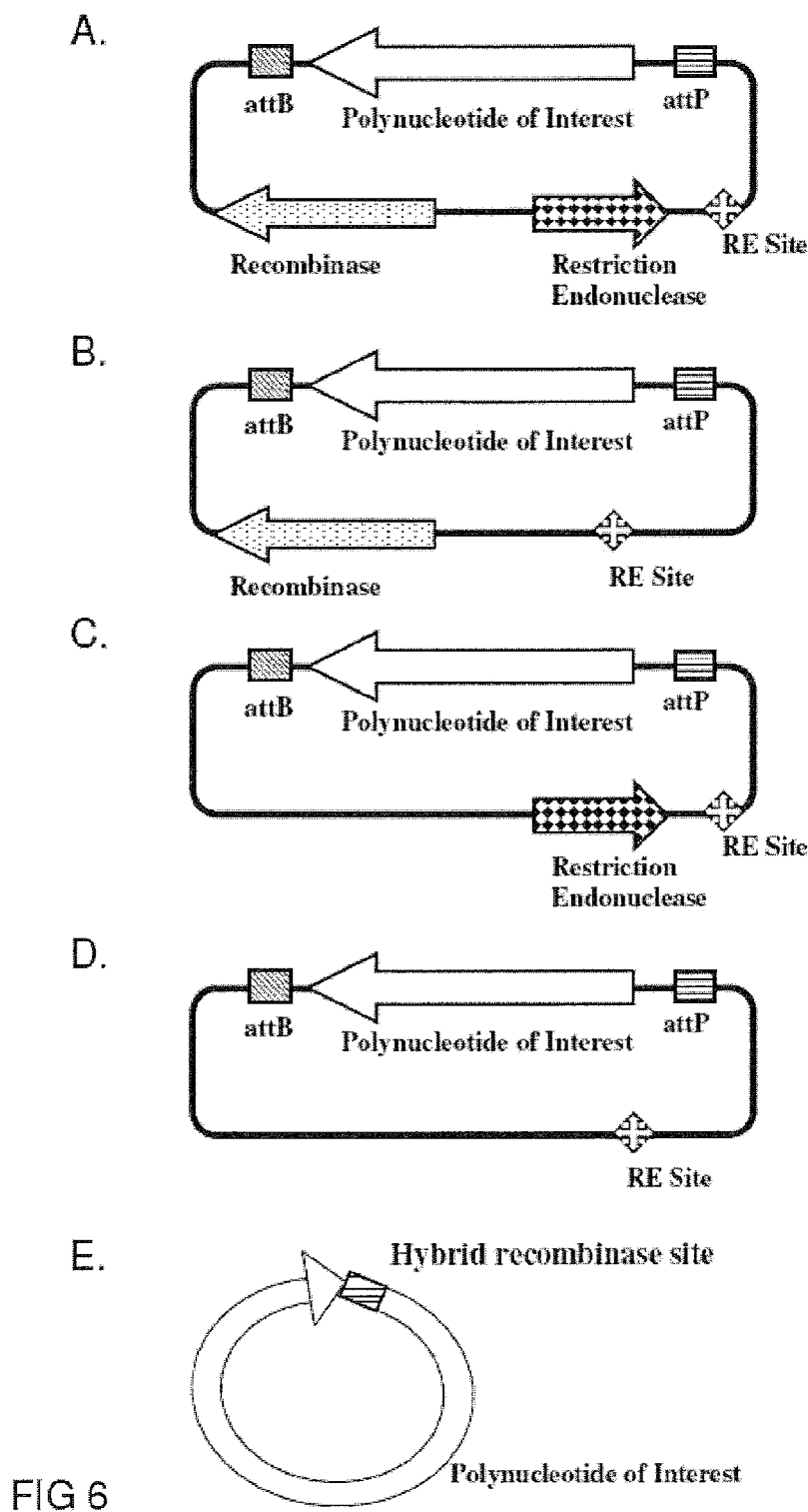
FIGS. 6A-6E show different embodiments of parental plasmids. Panel A shows a parental plasmid capable of expressing the recombinase and the restriction endonuclease. Panel B shows a parental plasmid capable of expressing the recombinase. Panel C shows a parental plasmid capable of expressing the restriction endonuclease. Panel D shows a parental plasmid with no coding sequence for the recombinase or endonuclease. Panel E shows the final minicircle vector following recombination.

The parent plasmid comprises at least a polynucleotide of interest flanked by attB and attP sites (which are recognized by a unidirectional site-specific recombinase), at least one restriction endonuclease site recognized by a restriction endonuclease not endogenous to the bacterial cell used to generate the minicircle vector, such as the rare-cutting restriction endonuclease IsceI; and sequences required for propagation and maintenance of the parent plasmid in a bacterial host, such as an origin of replication and optionally a nucleic acid sequence encoding a selectable marker (FIG. 6, panel A). In addition, the parent plasmid may comprise a nucleic acid sequence encoding araC, the repressor protein that blocks the BAD promoter from expressing nucleic acid sequences under its control in an uninduced condition. A coding sequence for the unidirectional site-specific recombinase, and a coding sequence for the restriction endonuclease is provided in the parent plasmid or in the bacterial cells.

It will be appreciated by one having skill in the art that a variety of restriction endonuclease can be used in the methods and compositions described here with the requirement that the restriction endonuclease is not endogenous to the bacterial cell. In some embodiments, the restriction endonuclease is a rare-cutting restriction endonuclease, including, but not limited to NotI, SfiI, NruI, MluI, SacII, SdaI, BssHII, I-TliI, I-CeuI, I-PpoI, I-SceI, I-PspI, and P1-Sce 1. In certain embodiments, the restriction endonuclease is I-SceI.

In order to produce the minicircle vectors, the parent plasmid is used to transfect the genetically modified bacterial cells; and the cells are grown to a desired density. Conditions are then provided that induce or otherwise allow expression of the recombinase. Upon contact of the parent plasmid with the recombinase, the attB and attP sites are recombined. The two products of the recombination are the minicircle vector, comprising the sequence of interest, and a hybrid recombination site; and a plasmid backbone circle comprising the prokaryotic backbone sequence of the parental plasmid, the at least one restriction endonuclease site, and a hybrid recombination site, such as an attL site or an attR site (FIG. 6, panel E). For example, in embodiments in which the minicircle nucleic acid vector comprises the attR site, the plasmid backbone circle will comprise the attL site. In embodiments in which the minicircle nucleic acid vector comprises the attL site, the plasmid backbone circle will comprise the attR site. Where the coding sequences for the recombinase and the restriction endonuclease are provided on the parental plasmid, these will be contained within the plasmid backbone circle.

Following the recombination of the attB and attP sites by the unidirectional site-specific recombinase, the bacterial culture conditions are altered for optimizing the restriction enzyme activity. The plasmid backbone bacterial DNA sequence circle and the residual parental plasmid will be digested by the restriction endonuclease at the restriction site(s) and subsequently degraded by bacterial endogenous exonucleases. As the only episomal circular DNA, the minicircle nucleic acid vector can then be isolated like standard plasmid from bacteria using conventional commercially available methods, such as by an affinity column. As a result, the minicircle vector will be free of plasmid backbone circles as well as unrecombined parental plasmid that would interfere with the use of the minicircle vectors in therapeutic, diagnostic, prophylactic or research applications.

In further embodiments, the bacterial cells used to generate the minicircle vectors will also include a genomically integrated sequence encoding a restriction endonuclease not endogenous to the bacterial cell, such as the rare-cutting restriction endonuclease IsceI, in addition to the coding sequence for the L-arabinose transporter araE gene under the control of a constitutive promoter and lacking in functional endonuclease I expression. In such embodiments, the parent plasmid is as described above, but does not include coding sequences for the restriction endonuclease not endogenous to the bacterial cell. The methods of production are as described above, where, following recombination; the coding sequences for the restriction endonuclease are present on the bacterial chromosome, not the plasmid backbone circle.

The benefit of this system is that the sequence encoding the restriction endonuclease not endogenous to the bacterial cell is not on a circular extrachromosomal vector present in the bacterial cell that could contaminate the minicircle nucleic acid vector preparation. In contrast, by providing the sequences encoding the restriction endonuclease as genomically integrated elements, the coding sequences will remain with the bacteria or in a linear fragment when the minicircle nucleic acid vector preparations are collected. If the sequence is present in the preparation as a linear DNA fragment, it is physically distinguishable from the minicircle. Consequently, the linear DNA fragment can be easily eliminated by conventional purification methods, even when contamination occurs. For example, lambda exonuclease can selectively digest linear DNA fragments without damaging minicircles.

In still further embodiments, the bacterial cells used to generate the minicircle vectors will include genomically integrated sequences encoding a unidirectional site-specific recombinase, such as øC31 integrase, and a restriction endonuclease not endogenous to the bacterial cell, such as the rare-cutting restriction endonuclease IsceI, in addition to the coding sequence for the L-arabinose transporter araE gene under the control of a constitutive promoter and lacking in functional endonuclease I expression. The methods of production are as described above, where, following recombination; the coding sequences for the restriction endonuclease and the recombinase are present on the bacterial chromosome, not the plasmid backbone circle.

The benefit of this system is that the sequences encoding the unidirectional site-specific recombinase and the restriction endonuclease not endogenous to the bacterial cell are not on an extrachromosomal vector present in the bacterial cell that could contaminate the minicircle nucleic acid vector preparation.

Regulatable Promoters

In certain embodiments, the nucleic acid sequences encoding the unidirectional site-specific recombinase and the restriction endonuclease are under the control of inducible promoters that provide for expression of the coding sequence only when the promoter is induced, such as the L-arabinose responsive inducible prompter araC-BAD. In such embodiments, the bacterial cells do not constitutively express the unidirectional site-specific recombinase and the restriction endonuclease. Instead, the unidirectional site-specific recombinase and the restriction endonuclease are expressed only when the inducible promoters are activated. Multiple copies of the unidirectional site-specific recombinase may be integrated into the genome.

In certain embodiments, the nucleic acid sequences encoding the unidirectional site-specific recombinase and the restriction endonuclease are under the control of two different inducible promoters. In such embodiments, the unidirectional site-specific recombinase is under the control of a first inducible promoter and the restriction endonuclease is under the control of a second inducible promoter. The two different inducible promoters allow for sequential expression of the unidirectional site-specific recombinase and the restriction endonuclease. For example, the unidirectional site-specific recombinase can be expressed first to provide for recombination of the attB and attP sites on the parental plasmid and produce minicircle nucleic acid vector, and then the restriction endonuclease can be expressed to allow for digestion of the plasmid backbone circle.

Regulatable promoters (i.e., derepressible or inducible) express genes of interest only under certain conditions that can be controlled. Derepressible elements are DNA sequence elements which act in conjunction with promoters and bind repressors (e.g. lacO/lacIq repressor system in *E. coli*). Inducible elements are DNA sequence elements which act in conjunction with promoters and bind inducers (e.g. gal1/gal4 inducer system in yeast). In either case, transcription is virtually "shut off" until the promoter is derepressed or induced by alteration of a condition in the environment (e.g., addition of IPTG to the lacO/lacIq system or addition of galactose to the gal1/gal4 system), at which point transcription is "turned-on."

Another type of regulated promoter is a "repressible" one in which a gene is expressed initially and can then be turned off by altering an environmental condition. In repressible systems transcription is constitutively on until the repressor binds a small regulatory molecule at which point transcription is "turned off". An example of this type of promoter is the tetracycline/tetracycline repressor system. In this system when tetracycline binds to the tetracycline repressor, the repressor binds to a DNA element in the promoter and turns off gene expression.

Examples of inducible prokaryotic promoters include the major right and left promoters of bacteriophage ($P_L$ and $P_R$), the trp, recA, lacZ, AraC and gal promoters of *E. coli*, the α-amylase (Ulmanen Ett at., J. Bacteriol. 162:176-182, 1985) and the sigma-28-specific promoters of *B. subtilis* (Gilman et al., Gene sequence 32:11-20(1984)), the promoters of the bacteriophages of *Bacillus* (Gryczan, In: The Molecular Biology of the Bacilli, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Unidirectional Site-Specific Recombinases

Two major families of unidirectional site-specific recombinases from bacteriophages and unicellular yeasts have been described: the integrase or tyrosine recombinase family includes Cre, Flp, R, and lambda integrase (Argos, et al., EMBO J. 5:433-440, (1986)) and the resolvase/invertase or serine recombinase family that includes some phage integrases, such as, those of phages øC31, R4, and TP901-1 (Hallet and Sherratt, FEMS Microbiol. Rev. 21:157-178 (1997)).

In certain embodiments, the unidirectional site-specific recombinase is a serine integrase. Serine integrases that may be useful for in vitro and in vivo recombination include, but are not limited to, integrases from phages øC31, R4, TP901-1, phiBT1, Bxb1, RV-1, A118, U153, and phiFC1, as well as others in the large serine integrase family (Gregory, Till and Smith, J. Bacteriol., 185:5320-5323 (2003); Groth and Calos, J. Mol. Biol. 335:667-678 (2004); Groth et al. PNAS 97:5995-6000 (2000); Olivares, Hollis and Calos, Gene 278: 167-176 (2001); Smith and Thorpe, Molec. Microbiol., 4:122-129 (2002); Stoll, Ginsberg and Calos, J. Bacteriol., 184:3657-3663 (2002)).

In general, site specific recombination sites recognized by a site-specific recombinase in a bacterial genome are designated bacterial attachment sites ("attB") and the corresponding site specific recombination sites present in the bacteriophage are designated phage attachment sites ("attP"). These sites have a minimal length of approximately 34-40 base pairs (bp) Groth, A. C., et al., Proc. Natl. Acad. Sci. USA 97, 5995-6000 (2000)). These sites are typically arranged as follows: AttB comprises a first DNA sequence attB5', a core region, and a second DNA sequence attB3' in the relative order attB5'-core region-attB3'; attP comprises a first DNA sequence (attP5'), a core region, and a second DNA sequence (attP3') in the relative order attP5'-core region-attP3'.

For example, for the phage øC31 attP (the phage attachment site), the core region is 5'-TTG-3' the flanking sequences on either side are represented here as attP5' and attP3', the structure of the attP recombination site is, accordingly, attP5'-TTG-attP3'. Correspondingly, for the native bacterial genomic target site (attB) the core region is 5'-TTG-3', and the flanking sequences on either side are represented here as attB5' and attB3', the structure of the attB recombination site is, accordingly, attB5'-TTG-attB3'.

Because the attB and attP sites are different sequences, recombination results in two hybrid site-specific recombination sites (designated attL or attR for left and right) that is neither an attB sequence or an attP sequence, and is functionally unrecognizable as a site-specific recombination site (e.g., attB or attP) to the relevant unidirectional site-specific recombinase, thus removing the possibility that the unidirectional site-specific recombinase will catalyze a second recombination reaction between the attL and the attR that would reverse the first recombination reaction. For example, after –, øC31 integrase-mediated a single site-specific recombination event takes place, the result is the following recombination product: attB5'-TTG-attP3'{φC31 vector sequences}attP5'-TTG-attB3'. Typically, after recombination the post-recombination recombination sites are no longer able to act as substrate for the øC31 recombinase since the bacterial strains used expressing neither the excisionase nor the co-factor(s) needed for the reverse reaction. Consequently, the recombination reaction can proceed to completion and result in a high yield of minicircle and, more importantly, a single population of minicircle comprising a monomer of the transgene expression cassette, which is the optimal structure for delivery and gene expression in vivo.

Minicircle Production Cells

The present invention also provides bacterial cells that are useful in the methods of the invention. In some embodiments, the cells have a genomically integrated polynucleotide cassette comprising a constitutive promoter to drive the expression of the L-arabinose transporter araE gene, and include a genetic mutation in the endA gene that results in the modified bacteria being unable to express functional endonuclease I. In such embodiments, the genetic mutation may be any mutation in the endA gene that results in knocking out the gene or production of non-functional endA. The genetic modification may be a deletion, inversion, or insertion in the endA coding sequence resulting in a non-functional endonuclease I. As such, no functional endonuclease I presents in the bacterium.

In other embodiments of the invention, the minicircle production cells are modified to constitutively express mutant LacY A177C. The lactose transporter mutant LacY A177C gains additional function to work as L-arabinose transporter, and by expressing this mutant the cells overcome the resistance to L-arabinose in sub-populations of bacteria (i.e., the all-or-none phenomenon).

Figure 7:
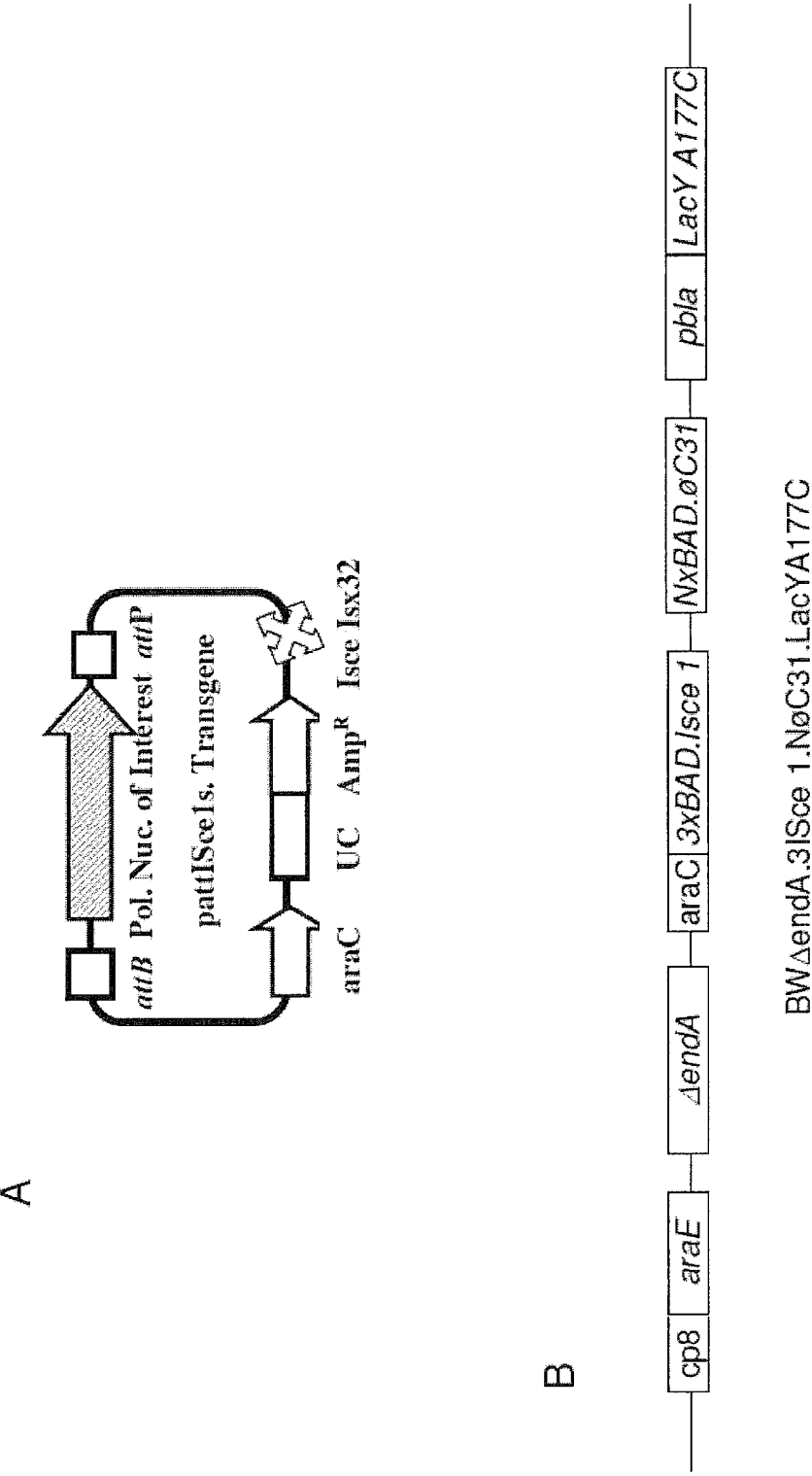
FIGS. 7A-7B show an embodiment of the invention. Panel A shows the minicircle parental plasmid construct; Panel B shows the corresponding bacterial strain with all the genetic alterations. pbla, promoter of beta-lactamase gene of *E. coli* derived from the plasmid pBlueScript of Stratagene (La Jolla, Calif.).

In further embodiments, the genetically modified bacteria include a genomically integrated coding sequence for a restriction endonuclease not endogenous to the bacteria, such as the rare-cutting restriction endonuclease IScel. In yet further embodiments, the genetically modified bacteria include at least one genomically integrated coding sequence for the unidirectional site-specific recombinase, such as øC31 integrase, as well as the restriction endonuclease not endogenous to the bacteria, such as the rare-cutting restriction endonuclease IScel (FIG. 7, panel B).

In certain embodiments, the nucleic acid sequences encoding the unidirectional site-specific recombinase and the restriction endonuclease are under the control of an inducible promoter. In such embodiments, the bacterial cells do not constitutively express the unidirectional site-specific recombinase and the restriction endonuclease. Instead, the unidirectional site-specific recombinase and the restriction endonuclease will only be expressed when the inducible promoters are activated.

In certain embodiments, the nucleic acid sequences encoding the unidirectional site-specific recombinase and the restriction endonuclease are under the control of two different inducible promoters. In such embodiments, the unidirectional site-specific recombinase is under the control of a first inducible promoter and the restriction endonuclease is under the control of a second inducible promoter. The two different inducible promoters allow for sequential expression of the unidirectional site-specific recombinase and the restriction endonuclease.

As noted above, the benefit of this system is that the sequences encoding the restriction endonuclease not endogenous to the bacterial cell and optionally the unidirectional site-specific recombinase are not on an extrachromosomal vector present in the bacterial cell that are hard to be removed when being co-isolated with the minicircle nucleic acid vector. In contrast, by providing the sequences encoding the restriction endonuclease not endogenous to the bacterial cell and optionally the unidirectional site-specific recombinase as genomically integrated elements, the coding sequences will remain with the bacteria when the minicircle nucleic acid vectors are collected or as linear DNA fragments that can be readily separated from the minicircles using conventional purification methods.

Bacterial expression systems and expression vectors containing regulatory sequences that direct high level expression of foreign proteins are well known to those skilled in the art. Any of these could be used to construct vectors for expression of the unidirectional site-specific recombinase and restriction endonuclease genes in bacteria. These vectors could then be introduced into the bacteria via transformation and subsequent genomic integration to allow for expression of high level of the non-endogenous, or foreign, enzymes.

Vectors or cassettes useful for the transformation of suitable bacterial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Stable expression can be achieved by integrating a construct into the host genome. The construct can be integrated at a random site within the bacterial host genome or be targeted to a selected locus through the use of constructs containing regions of homology with the locus in host genome. Where constructs are targeted to an endogenous locus, all or some of the transcriptional regulatory regions can be provided by the endogenous locus. Stable expression of the gene of interest can be achieved through the use of a selectable marker in the expression construct, followed by selection for cells expressing the marker after integration.

Minicircle DNA Administration

The subject methods find use in a variety of applications in which it is desired to generate minicircle nucleic acid preparations that are substantially free of contaminating nucleic acids and to introduce the exogenous minicircle nucleic acid sequence into a target cell, and particularly of interest where it is desired to express a polynucleotide of interest in a target cell. As mentioned above, the subject vectors may be administered by in vitro or in vivo protocols.

The target cell may be an individual cell, e.g., as may be present in an in vitro environment, or present in a multicellular organism. As such, the subject methods of introducing the minicircle nucleic acid vectors may be in vivo methods, by which is meant that the exogenous nucleic acid is administered directly to the multicellular organism either systemically or in a localized manner to specific tissues or cells, such as localized delivery of the minicircle vectors to hepatic cells, or in vitro methods, in which the target cell or cells are removed from the multicellular organism and then contacted with the exogenous nucleic acid.

As indicated above, the subject vectors can be used with a variety of target cells, where target cells in many embodiments are non-bacterial target cells, and often eukaryotic target cells, including, but not limited to, plant and animal target cells, e.g., insect cells, vertebrate cells, particularly avian cells, e.g., chicken cells, fish, amphibian and reptile cells, mammalian cells, including murine, porcine, ovine, equine, rat, ungulates, dog, cat, monkey, and human cells, and the like.

In the methods of the subject invention, the vector is introduced into the target cell. Any convenient protocol may be employed, where the protocol may provide for in vitro or in vivo introduction of the vector into the target cell, depending on the location of the target cell. For example, where the target cell is an isolated cell, the vector may be introduced directly into the cell under cell culture conditions permissive of viability of the target cell, e.g., by using standard transformation techniques. Such techniques include, but are not necessarily limited to: viral infection, transformation, conjugation, protoplast fusion, electroporation, particle gun technology, calcium phosphate precipitation, direct microinjection, viral vector delivery, use of nanoparticles, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the targeting vector may be administered to the organism or host in a manner such that the targeting construct is able to enter the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body. Methods for the administration of nucleic acid constructs are well known in the art and include use of nanoparticles as described in Bharali et al., "Organically Modified Silica Nanoparticles: A Nonviral Vector for In Vivo Gene Delivery and Expression in the Brain" PNAS 102(32):11539-44 (2005). Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995,), using viral vectors (Monahan, et al, Gene Therapy 4:40-49, 1997; Onodera, et al, Blood 91:30-36, 1998,), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 pl).

The route of administration of the vector to the multicellular organism depends on several parameters, including: the nature of the vectors that carry the system components, the nature of the delivery vehicle, the nature of the multicellular organism, and the like, where a common feature of the mode of administration is that it provides for in vivo delivery of the vector components to the target cell(s) via a systemic route. Of particular interest as systemic routes are vascular routes, by which the vector is introduced into the vascular system of the host, e.g., an artery or vein, where intravenous routes of administration are of particular interest in many embodiments.

Any suitable delivery vehicle may be employed, where the delivery vehicle is typically a pharmaceutical preparation that includes an effective amount of the vector present in a pharmaceutically acceptable carrier, diluent and/or adjuvant, or complexed covalently or non-covalently to a nanoparticle. In certain embodiments, the vector is administered in an aqueous delivery vehicle, e.g., a saline solution. As such, in many embodiments, the vector is administered intravascularly, e.g., intraarterially or intravenously, employing an aqueous based delivery vehicle, e.g., a saline solution.

In many embodiments, the vector is administered to the multicellular organism in an in vivo manner such that it is introduced into a target cell of the multicellular organism under conditions sufficient for expression of the nucleic acid present on the vector to occur. A feature of the subject methods is that they result in persistent expression of the nucleic acid present thereon, as opposed to transient expression, as indicated above. By persistent expression is meant that the expression of nucleic acid at a detectable level persists for an extended period of time, if not indefinitely, following administration of the subject vector. By extended period of time is meant at least 1 week, usually at least 2 months and more usually at least 6 months. By detectable level is meant that the expression of the nucleic acid is at a level such that one can detect the encoded protein or the non-translated RNA in the cell and/or mammal, e.g., in the serum of the mammal, at detectable levels at a therapeutic concentration, or has the desired biological effect expected with expression, as compared to a control in which a pBluescript vector is employed, nucleic acid expression persists for a period of time that is at least about 2 fold, usually at least about 5 fold and more usually at least about 10 fold longer following the subject methods as compared to a control.

A feature of many embodiments of the subject methods is that the above-described persistent expression is achieved without integration of the minicircle nucleic acid vectors into the target cell genome of the host. As such, the minicircle nucleic acid vectors introduced into the target cells does not integrate into, i.e., insert into, the target cell genome, i.e., one or more chromosomes of the target cell. Accordingly, the vectors are maintained episomally, such that they are episomal vectors that provide for persistent expression.

The particular dosage of vector that is administered to the multicellular organism in the subject methods varies depending on the nature of vector, the nature of the expression module and gene, the nature of the delivery vehicle and the like. Dosages can readily be determined empirically by those of skill in the art. For example, in mice where the vectors are intravenously administered in a saline solution vehicle, the amount of vector that is administered in many embodiments typically ranges from about 2 to 100 and usually from about 10 to 50 µg. The subject methods may be used to introduce nucleic acids of various sizes into the target cell.

In in vivo protocols, the subject methods may be employed to introduce a nucleic acid into a variety of different target cells. Target cells of interest include, but are not limited to: muscle, brain, endothelium, hepatic, and the like. Of particular interest in many embodiments is the use of the subject methods to introduce a nucleic acid into at least a hepatic cell of the host.

Utility

The subject methods find use in a variety of applications in which the production and introduction of a nucleic acid into a target cell is desired. Applications in which the subject vectors and methods find use include: research applications, polypeptide synthesis applications, RNA interference applications, and therapeutic applications. Each of these representative categories of applications is described separately below in greater detail.

Research Applications

Examples of research applications in which the subject nucleic acids produced by the subject methods include applications designed to characterize a particular gene. In such applications, the subject vector is employed to introduce and express a gene of interest in a target cell and the resultant effect of the inserted gene on the cell's phenotype is observed. In this manner, information about the gene's activity and the nature of the product encoded thereby can be deduced. One can also employ the subject methods to produce models in which overexpression and/or misexpression of a gene of interest is produced in a cell and the effects of this mutant expression pattern are observed.

Polypeptide Synthesis Applications

In addition to the above research applications, the subject nucleic acids produced by the subject methods also find use in the synthesis of polypeptides, e.g. proteins of interest. In such applications, a minimal plasmid vector that includes a gene encoding the polypeptide of interest in combination with requisite and/or desired expression regulatory sequences, e.g. promoters, etc., (i.e. an expression module) is introduced into the target cell, via in vivo administration to the multicellular organism in which the target cell resides, that is to serve as an expression host for expression of the polypeptide. Following in vivo administration, the multicellular organism, and targeted host cell present therein, is then maintained under conditions sufficient for expression of the integrated gene. The expressed protein is then harvested, and purified where desired, using any convenient protocol.

As such, the subject methods provide a means for at least enhancing the amount of a protein of interest in a multicellular organism. The term 'at least enhance' includes situations where the methods are employed to increase the amount of a protein in a multicellular organism where a certain initial amount of protein is present prior to in vivo administration of the vector. The term 'at least enhance' also includes those situations in which the multicellular organism includes substantially none of the protein prior to administration of the vector. By "at least enhance" is meant that the amount of the particular protein present in the host is increased by at least about 2 fold, usually by at least about 5 fold and more usually by at least about 10 fold. As the subject methods find use in at least enhancing the amount of a protein present in a multicellular organism, they find use in a variety of different applications, including agricultural applications, pharmaceutical preparation applications, and the like, as well as therapeutic applications, described in greater detail infra.

RNA Interference Applications

In addition to the above protein synthesis applications, the subject minicircle nucleic acid vector produced by the subject methods also find use in RNA interference applications of sequence-specific post-transcriptional silencing of gene expression mediated by small single or double-stranded RNA including shRNA, siRNA, RNA decoys, ribozymes, or antisense RNA or others. In such embodiments the polynucleotide of interest comprises a coding sequence that provides for expression of non-translated RNA products, e.g., shRNA as described in McCaffery et al., "RNA interference in adult mice", Nature 418(6893):38-9 (2002), Paskowitz et al., "Rapid and stable knockdown of an endogenous gene in retinal pigment epithelium", Hum Gene Ther. 18(10):871-80 (2007), antisense RNA, as described in Lieber et al., "Elimination of hepatitis C virus RNA in infected human hepatocytes by adenovirus-mediated expression of ribozymes," J Virol. (1996 December) 70(12):8782-91; Lieber et al., "Related Articles Adenovirus-mediated expression of ribozymes in mice," J Virol. (1996 May) 70(5):3153-8; Tang et al., "Intravenous angiotensinogen antisense in AAV-based vector decreases hypertension," Am J Physiol. (1999 December) 277(6 Pt 2):H2392-9; Horster et al. "Recombinant AAV-2 harboring gfp-antisense/ribozyme fusion sequences monitor transduction, gene expression, and show anti-HIV-1 efficacy, Gene Ther. (1999 July) 6(7):1231-8; and Phillips et al., "Prolonged reduction of high blood pressure with an in vivo, nonpathogenic, adeno-associated viral vector delivery of AT1-R mRNA antisense," Hypertension. (1997 January) 29(1 Pt 2):374-80. As such, the subject methods can be used to deliver therapeutic non-translated RNA molecules, e.g., shRNA, antisense RNA, etc., into target cells of the host.

Therapeutic Applications

The subject nucleic acids produced by the subject methods also find use in therapeutic applications, in which the vectors are employed to introduce a therapeutic nucleic acid, e.g., gene or a non-translated RNA such as a shRNA, into a target cell, i.e., in gene therapy applications, to provide for persistent expression of the product encoded by the nucleic acid present on the vector. The subject vectors may be used to deliver a wide variety of therapeutic nucleic acids, including nucleic acid encoding proteins or non-translated RNAs. Therapeutic nucleic acids of interest include genes that replace defective genes in the target host cell, such as those responsible for genetic defect based diseased conditions; genes which have therapeutic utility in the treatment of cancer; and the like. Therapeutic nucleic acids of interest also include nucleic acid sequences encoding RNAs, such as double-stranded RNAs or shRNAs that mediate sequence-specific post-transcriptional silencing of gene expression in a target cell.

Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductor regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like, where the particular coding sequence of the above proteins that is employed will generally be the coding sequence that is found naturally in the host being treated, i.e., human coding sequences are employed to treat human hosts. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

An important feature of the subject methods, as described supra, is that the subject methods may be used for in vivo gene therapy applications. By in vivo gene therapy applications is meant that the target cell or cells in which expression of the therapeutic gene is desired are not removed from the host prior to contact with the vector system. In contrast, the subject vectors are administered directly to the multicellular organism and are taken up by the target cells; then expressed in the target cell. Another important feature is that the resultant expression is persistent and occurs without integration of the vector DNA into the target cell genome.

Kits

Also provided by the subject invention are kits for use in practicing the subject methods of producing minicircle nucleic acid delivery to target cells as well as methods of introducing the vectors into a target cell.

In some embodiments, the subject kits will include bacterial cells comprising a genomically integrated coding sequence for the L-arabinose transporter araE gene under the control of a constitutive promoter and lacking functional endonuclease I expression. In certain embodiments, the subject kits include such bacterial cells, and further include a minicircle parental plasmid comprising either a restriction endonuclease site for insertion of a polynucleotide of interest, where the polynucleotide of interest is flanked by attB and attP sites recognized by a unidirectional site-specific recombinase. The parental plasmid further comprises a coding sequence for the unidirectional site-specific recombinase, a coding sequence for a restriction endonuclease not endogenous to the bacterial cell, and at least one restriction site recognized by the encoded restriction endonuclease to provide for destruction of the plasmid backbone circle following the recombination reaction. The vector may be present in an aqueous medium or may be lyophilized.

In some embodiments, the subject kits will include bacterial cells which will include a genomically integrated sequence encoding a restriction endonuclease not endogenous to the bacterial cell, such as the rare-cutting restriction endonuclease ISceI, in addition to the coding sequence for the L-arabinose transporter araE gene under the control of a constitutive promoter and lacking in functional endonuclease I expression. In certain embodiments, the subject kits include the bacterial cells and minicircle parental plasmid as described above.

In some embodiments, the subject kits will include bacterial cells expressing a unidirectional site-specific recombinase and a restriction endonuclease not endogenous to the bacterial cell in addition to the coding sequence for the L-arabinose transporter araE gene under the control of a constitutive promoter and lacking in functional endonuclease I expression, as described in greater detail above. In some embodiments, the subject kits will include bacterial cells expressing the additional L-arabinose transporter LacY A177C under the control of a constitutive promoter. In certain embodiments, the subject kits generally include the bacterial cells and minicircle parental plasmid as described above.

The subject kits may further include an aqueous delivery vehicle, e.g. a buffered saline solution, etc. In addition, the kits may include one or more restriction endonucleases for use in transferring a nucleic acid of interest into the minicircle parental plasmid, where the restriction endonuclease will correspond to the restriction endonuclease site present on the minicircle parental plasmid. In the subject kits, the above components may be combined into a single aqueous composition for delivery into the host or separate as different or disparate compositions, e.g., in separate containers. Optionally, the kit may further include a vascular delivery means for delivering the aqueous composition to the host, e.g. a syringe etc., where the delivery means may or may not be pre-loaded with the aqueous composition.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

Plasmids. Construction of minicircle producing plasmid p2øC31.hFIX (FIG. 1, panel A) was described earlier (Chen Z Y et al., Human Gene Therapy 16:126, 2005); the MC.hFIX (FIG. 1, panel B) and the plasmid BB (FIG. 1, panel C) were the recombination products derived from the minicircle producing plasmid p2øC31.hFIX. We made the curable plasmid p2øC31.ISce 1g&s (FIG. 1, panel D) by eliminating the attB-hFIX-attP sequence from the plasmid p2øC31.hFIX. To make the plasmid pKanR.endA (FIG. 1, panel E), we replaced the hFIX cassette in p2øC31.hFIX with the kanamycin resistance gene derived from plasmid pBK-CMV and relocated the attB-Kanamycin-attP sequence into the pBlueScript (Stratagene, La Jolla, Calif.) and generated the intermediate plasmid pKanR; subsequently, we PCR-generated the up- and downstream targeting sequences using endA-specific primers and Top 10 genomic DNA as template and inserted them outside the attB- and attP-site, respectively. We constructed the p3BAD.ISce Ig.KanR.UMU (FIG. 1, panel F) by inserting three tandem copies of the BAD.ISce I cassette, which was derived from the plasmid p2øC31.hFIX (FIG. 1, panel A), upstream of the attB site of the intermediate plasmid pKanR, and the two UMU-targeting sequences generated by PCR using UMU gene-specific primers and Top 10 genomic DNA.

We made the plasmid p8ISce Is (FIG. 1, panel G) by inserting eight consecutive ISce I restriction sites, each encoded by a pair of DNA oligomers, into the Kpn I site of the pBlueScript. Plasmids pcI857.FLP and −pBAD.RED were gifts from Dr. Wanner B L, Yale University (PNAS 97:6640, 2000). øC31, phage *Streptomyces* recombinase gene; hFIX, human coagulation protein factor IX; attB, bacterial attachment sequence; attP, phage attachment sequence; attR and attL, the right and left hybrid sequences, respectively; ISce Ig, the gene encoding the restriction enzyme ISce I; ISce Is, the ISce I restriction site; sApoE, the artificial enhancer/promoter described in details earlier (Miao et al. Mol Ther 1:522, 2000); AmpR, ampicillin resistance gene; UC, pUC plasmid replication origin; BDA, BAD promoter; araC, araC repression gene; L-arab, L-arabinose.

Figure 3:
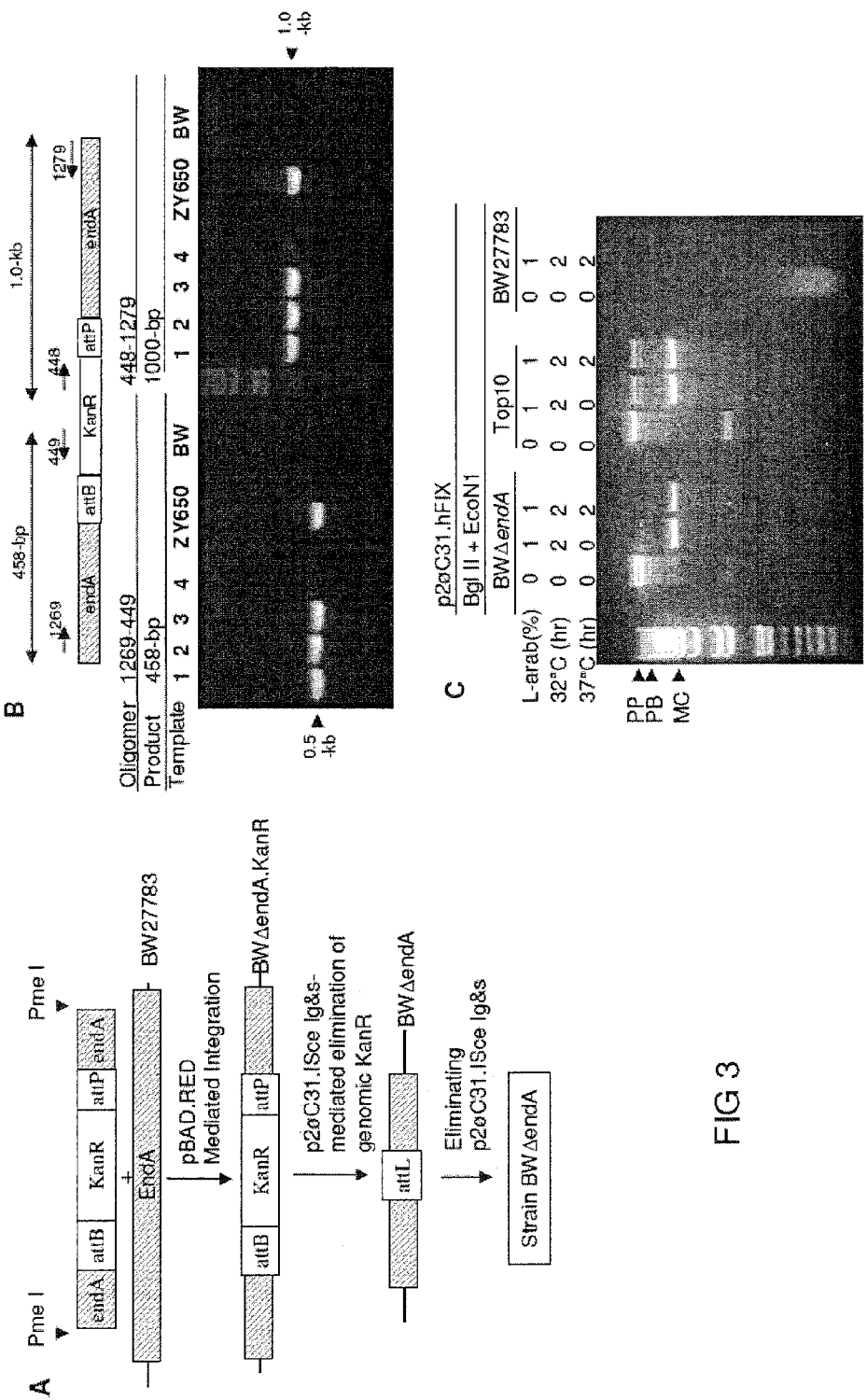
FIGS. 3A-3C show overcoming DNA degradation problems by deleting the endA gene. Panel A shows the flow chart illustrating the endA-deleting procedure. We prepared the DNA fragment including the two endA-targeting sequences from plasmid pKanR.endA (FIG. 1, panel E) by Pme 1 digestion and used it to inactivate the endA gene of BW27783 following the protocol of Datsenko and Wanner B L (PNAS 97:6640, 2000). Briefly, we transformed a colony of BW27783 with plasmid pBAD.RED, and induced the expression of the phage lambda RecBCD recombination enzyme complex by culturing a colony of the resulted bacteria in LB containing 1% L-arabinose at 30° C. until OD600 reading was about 0.5; we transformed the resulted competent cells with the linear targeting DNA fragment, and selected the kanamycin-resistant colonies for further analysis. Plasmid pBAD.RED was eliminated from the resulted BWendA-.KanR cells by incubating the cells at 43° C. overnight. To eliminate the kanamycin-resistance gene from the genome, the intermediate strain BWendA.KanR were transformed with plasmid p2øC31.ISce Ig&s (FIG. 1, panel D); subsequently, a colony of the transformed cells were incubated in LB broth with 1% L-arabinose to induce the expression of both øC31 and ISce 1 enzymes, resulting in the loss of the kanamycin resistance gene through the øC31-mediated recombination between the attB and attP and the cure of the plasmid p2øC31.ISce Ig&s through ISce I-mediated restriction simultaneously. The ampicillin- and kanamycin-sensitive colonies were selected for further characterization. Panel B shows confirming DNA integration. Integration of the kanamycin-resistant gene was confirmed by PCR assay using two pairs of primers, each comprising one at the kanamycin gene (primers 448 or 449) and the other at the endA (primers 1269 or 1279). Expected PCR products, 0.5- and 1.0-kb in size, respectively, in 3 out of 4 colonies examined. BW, BW27783 genome; ZY650, plasmid pKanR.endA (FIG. 1, panel E). Panel C shows confirming the loss of endonuclease 1 activity. Minicircle MC.hFIX was produced using the resulted strains BWΔendA and Top 10, cut with Bgl II plus EncoN1, each cuts once through the minicircle or the plasmid BB, and analyzed via gel electrophoresis.

Engineering bacterium. We obtained the bacterial strain BW27783 from Dr. Keasling J D of University of California in Berkeley (Khlebnikov A et al., Microbiology 147:3241, 2001). To make the intermediate strain BWΔendA.KanR (FIG. 3, panel A), we prepared the endA-targeting DNA fragment from plasmid pKanR.endA (FIG. 1, panel E) via Pme 1 digestion; we integrated it into the endA locus in BW27783 and cured the plasmid pBAD.RED following the procedure of Datsenko K A and Wanner B L (PNAS 97:6640, 2000). Subsequently, we ran two PCR reactions using gene-specific primers and found PCR products with expected size from the new strain genome, suggesting the targeted integration of the antibiotic resistance gene (FIG. 3, panel B). To eliminate the kanamycin-resistance gene from BWΔendA.KanR, we transformed the strain BWΔendA.KanR with plasmid p2øC31.ISce 1g&s, inoculated a colony in LB broth containing 1% L-arabinose, and incubated at 30° C. for four hours; subsequently, we selected the ampicillin- and kanamycin-sensitive colonies by growing bacterial colonies at agar plates with or without either antibiotics (FIG. 3, panel A).

To determine if the endonuclease 1 was inactivated, we transformed the resulted strain BWΔendA with plasmid p2øC31.hFIX, generated minicircle using standard protocol, and found that the minicircle was intact, further confirming the deletion of the endA gene (FIG. 3, panel C). Using the targeting DNA generated from plasmid p3BAD.ISce I.Kan-R.UMU (FIG. 1, panel F) and following the same procedure we integrated 3 tandem copies of the BAD.ISce 1 gene into the genome of strain BWΔendA and generated the new strain BWΔendA.3ISce 1g.

Minicircle Production Procedure.

We produced minicircle according to the procedure described previously (Chen et al., Human Gene Therapy 16:126, 2005). Briefly, we used p2øC31.hFIX to transform Top 10 or other strains, and grew a colony of the bacteria in LB. We spun down the bacteria from the overnight culture, resuspended 4:1 (volume of overnight bacterial culture vs volume of fresh broth for resuspension) in fresh LB broth with 1% of L-arabinose, and incubated the reaction at 30° C. with shaking at 250 rpm for two hours. Subsequently, we added half volume of fresh LB broth (pH8.0) with 1% L-arabinose to the induction reaction and continued the incubation at 37° C. for additional two hours. We isolated the minicircle MC.FIX from bacteria using Qiagen plasmid purification kits (Qiagen, Valencia, Calif.).

Example 1

Reduction of Impurity DNA in Minicircle Preparation from BW27783

In our original protocol, we used minicircle-producing plasmid such as p2øC31.hFIX (FIG. 1, panel A) and Top 10 strain to produce minicircle (Chen Z Y et al., Human Gene Therapy 16:126, 2005). In our minicircle prep, however, we detected small but variable amount of impurity DNA comprising the unrecombined parental plasmid and the plasmid backbone circle (plasmid BB). We perceived that the impurity DNAs were largely resulted from the "all-or-none" phenomenon: a subpopulation of the bacteria became incapable of expressing the high-capacity, low-affinity L-arabinose transporter araE and absorbing L-arabinose and expressing øC31 and ISce I genes under the control of the araC-ABD regulation system. Khlebnikov A and colleagues (Microbiology 147:3241, 2001) reported the partial overcoming of the "all-or-none" phenomenon by using the constitutive promoter cp8 to drive the expression of araE in strain BW27783. In an attempt to solve the impurity DNA problem, we replaced the native promoter with the same cp8 promoter to drive the expression of the araE gene in Top 10 strain. There was no change in minicircle yields or contamination perhaps because the DNA sequences were not correctly inserted.

Figure 2:
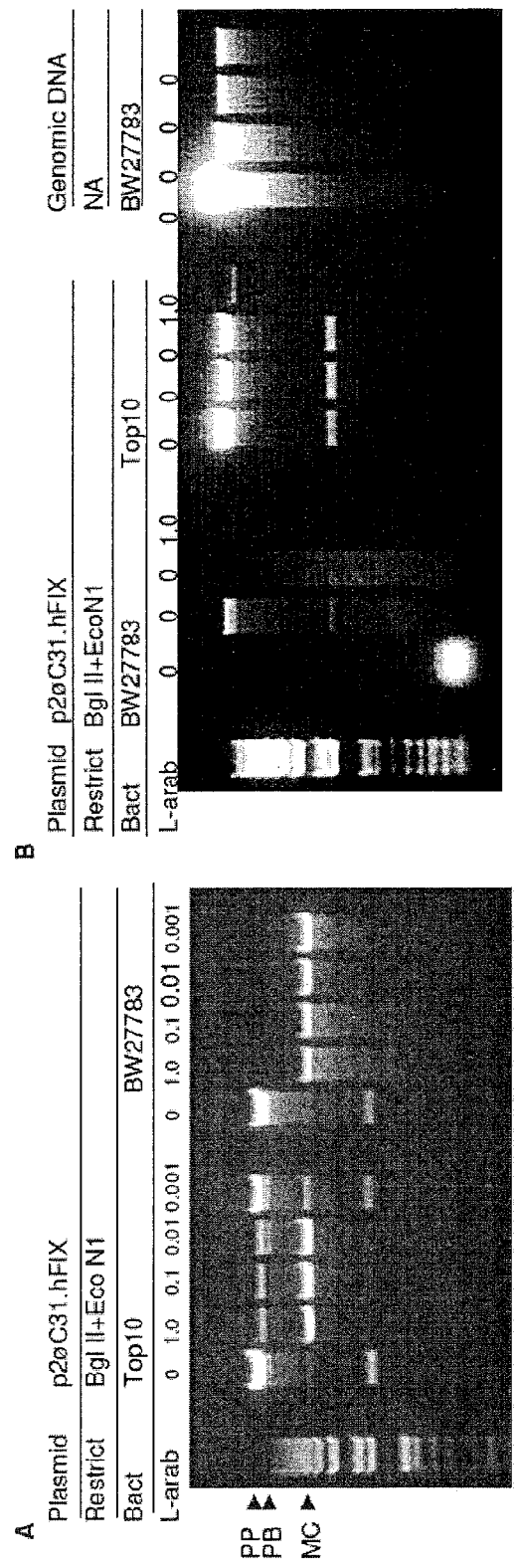
FIGS. 2A-2B show that the BW27783 strain eliminated impurity but degraded the DNA. Panel A shows elimination of impurity DNAs. Minicircle was produced using plasmid p2øC31.hFIX with either strain BW27783 or Top 10 and the protocol described earlier (Chen et al., Human Gene Therapy 16:126, 2005); the minicircle quality was determined by agarose gel assay after the DNA was digested with Bgl II plus EcoN1. The impurity DNAs comprising the parental plasmid (PP) and the plasmid BB (PB) were evident in the minicircle produced from Top 10 strain, but invisible from BW27783, even when the concentration of the inducer L-arabinose was as low as 0.001% in the culture. Restrict., restriction; Bact., bacterial strain; L-arab., L-arabinose. Panel B shows DNA degradation. DNA degradation was evident in samples of plasmid and minicircle and bacterial genome prepared from BW27783, but absent in that from Top 10 strain.

In addition we obtained the BW27783 from Dr. Keasling of University of California in Berkeley and used it to replace Top 10 to make minicircle; we found that the minicircle the strain produced contained no visible impurity DNA as determined by agar gel electrophoresis, and that this was achievable when the concentration of the arac-pBAD inducer L-arabinose was as low as 0.001% in incubation reaction, a level 1,000-fold lower than that in Top 10 strain (FIG. 2, panel A). Unexpectedly, we found variable degrees of minicircle DNA degradation (FIG. 2, panel B).

Example 2

Deletion of EndA Gene Overcame DNA Degradation Problem

As recA is known to affect plasmid stability (Khlebnikov A et al., J Bacteriol 182:7029, 2000), we inactivated the recA gene in BW27783, but found it was not helpful (data not shown). Perceiving that the endonuclease 1 was responsible, we set forth to delete the endA gene encoding this DNA-destructive enzyme. To do this, we made the plasmid pkan-R.endA carrying the kanamycin resistance gene flanked by attB and attP sites and two PCR-generated sequences targeting the endA gene (FIG. 1, panel E); we prepared the linear targeting DNA by cutting the plasmid with Pme 1 and integrated it to the endA gene of BW27783 following the protocol of Datsenko K A and Wanner B L (PNAS 97:6640, 2000) with modifications (FIG. 3, panel A). We failed in the first attempt by using two 35-bp sequences for targeting as suggested (data not shown); however, we succeeded later by increasing the targeting sequences to 329- and 754-bp, respectively. We detected the integrated DNA in 3 out of 4 resulted bacterial colonies via PCR using kanamycin resistance gene- and endA-specific primers (FIG. 3, panel B). We removed the kanamycin resistance gene from bacterial genome by expressing øC31 recombinase from plasmid p2øC31.ISce 1g&s (FIG. 1, panel D) to mediate the recombination between attB and attP and obtained the strain BWΔendA (FIG. 3A).

Figure 9:
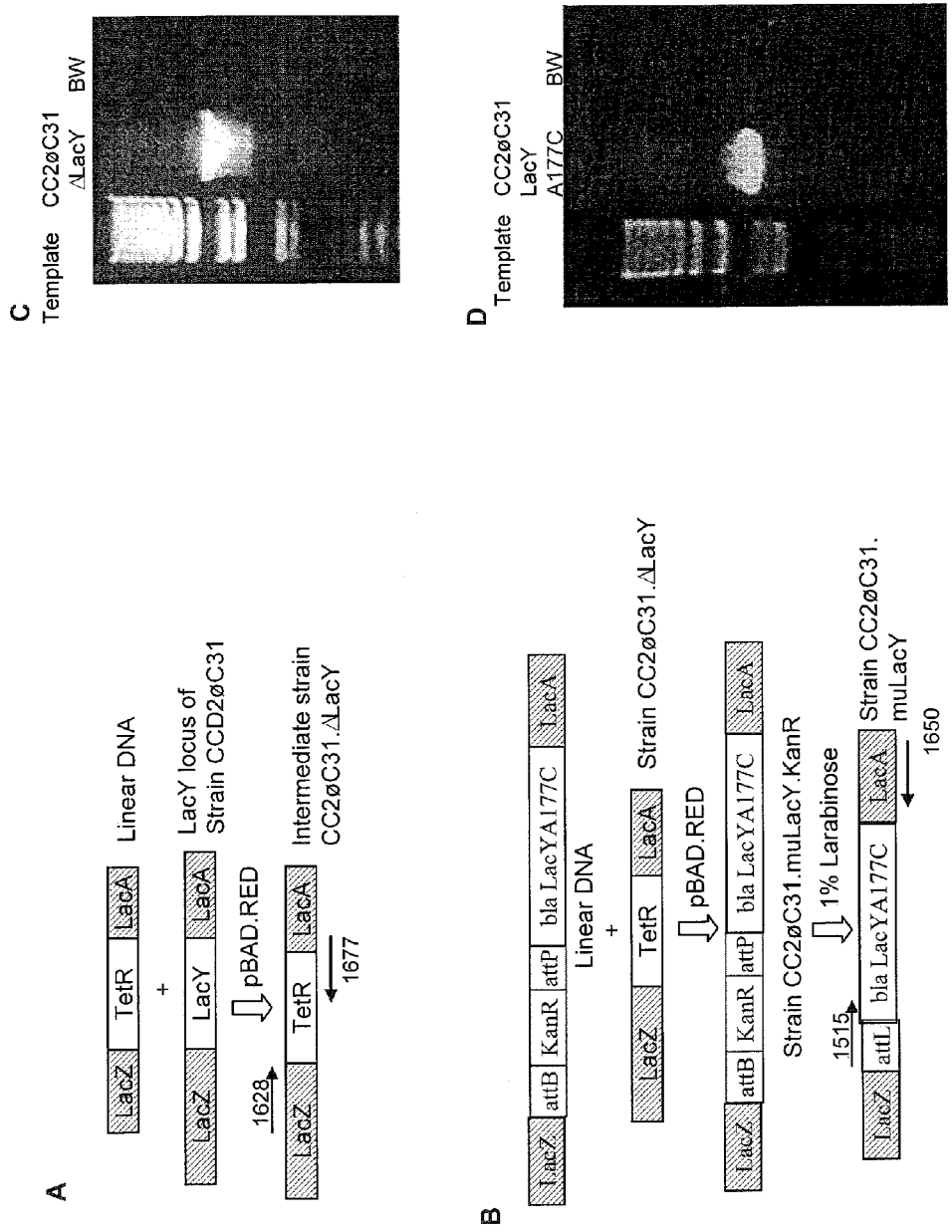
FIGS. 9A-9D show the integration of a $2^{nd}$ L-arabinose transporter gene. Flowchart
Figure 10:
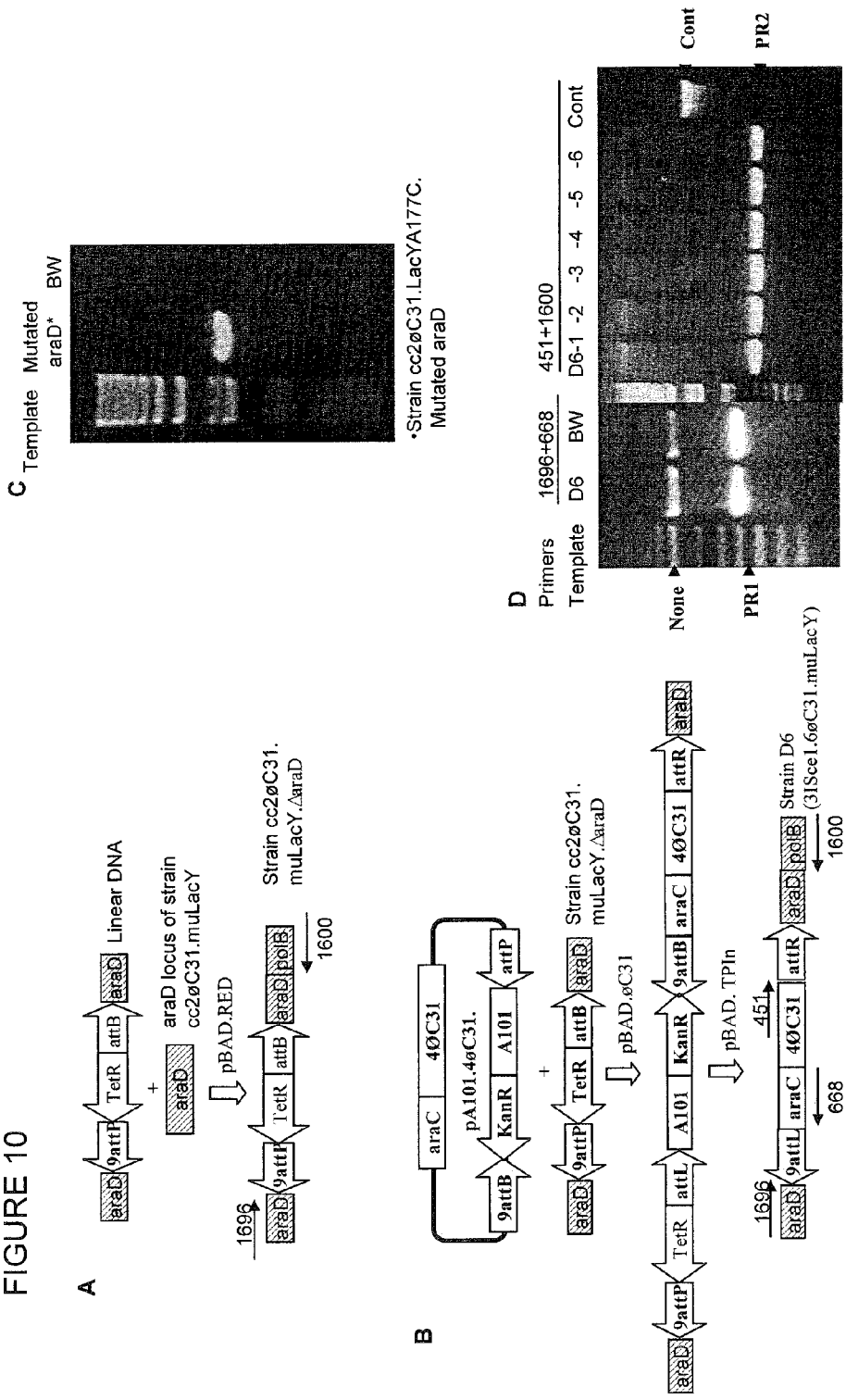
FIG. 10A-10D show the integration of 4 tandem copies of the BAD.øC31 cassette.
Figures 11, 11B:
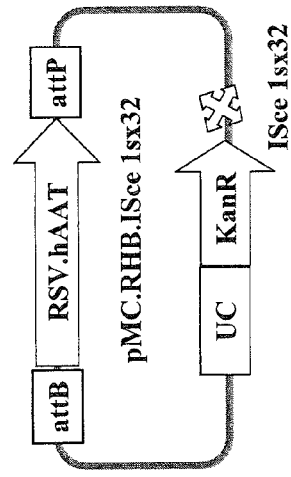
Figure 12:
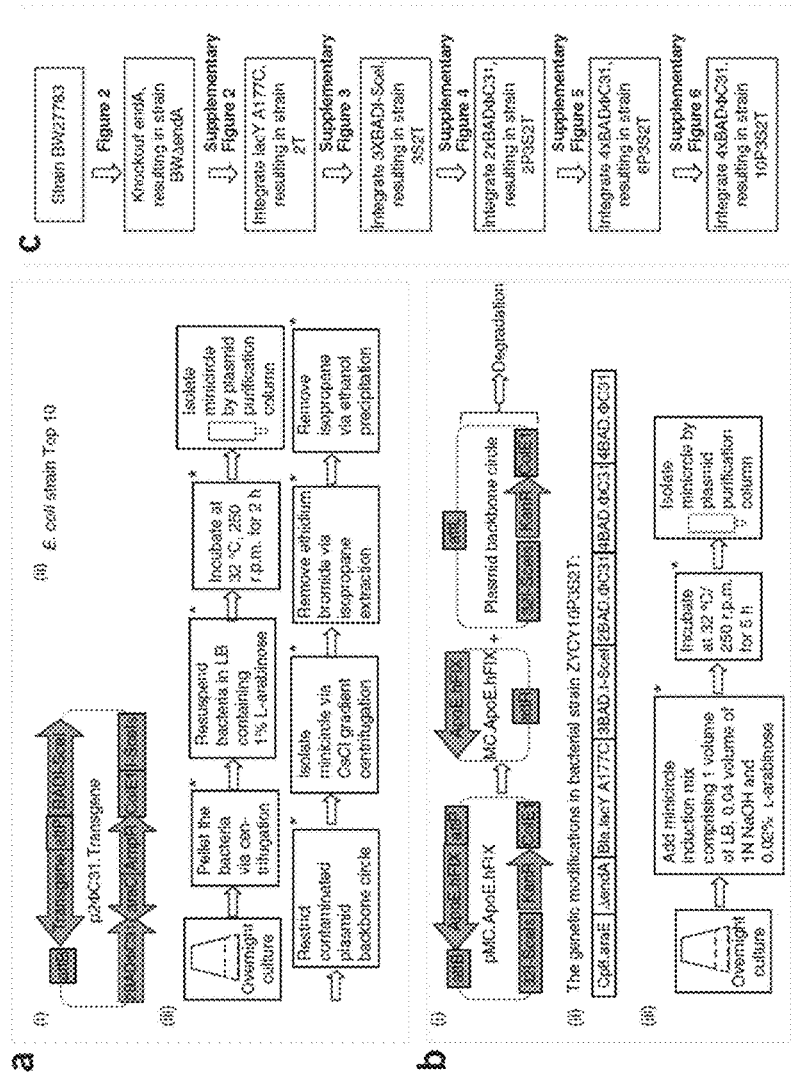
FIGS. 12A-12C. Comparison of the present and previous minicircle systems. (a) An earlier version of the minicircle production system. (i) Structure of the previous minicircle producer plasmid. BAD and araC, the promoter and the repressor gene of the inducible $_{I}$-arabinose-araC.BAD system; φC31, bacteriophage φC31 integrase gene; attB and attP, the bacterial and phage attachment sites of the φC31 integrase; I-SceI, I-SceI homing endonuclease gene; I-SceIs, the I-SceI recognition site; AmpR, ampicillin resistance gene; ColE1, DNA replication origin. (ii) E. coli strain Top10, original strain used to produce minicircle. (iii) Flow chart showing the minicircle production protocol. Each box represents a major step and the starred boxes represent the steps required in addition to a routine plasmid production protocol. (b) The present minicircle system. (i) Diagram of a minicircle producer plasmid and its conversion to minicircle DNA. pMC.ApoE.hFIX, minicircle producer plasmid; hFIX, human factor IX; sApoE, promoter/enhancer, as described previously$_1$; KanR, kanamycin resistance gene. Upon $_{I}$-arabinose induction, φC31 is expressed to mediate the formation of minicircle and plasmid backbone circle and I-SceI to induce the destruction of plasmid backbone circle. (ii) The genetic modifications of the minicircle producing bacterial strain ZYCY10P3S2T. 10P3S2T stands for (1) ten copies of BAD.φC31 cassette, that were integrated in three loci of the bacterial genome: two tandem copies at the ΔendA locus, and four copies at the araD and galK each; (2) three tandem copies of BAD.I-SceI cassette, which were integrated at UMU locus and (3) two genes constitutively expressing $_{I}$-arabinose transporter, one was araE gene driven by an artificial promoter cp8, which presented in strain BW27783 (ref. 10); the other was the bla-lacY A177C cassette, which was integrated at the lacY locus; bla, beta-galactosidase gene promoter; lacY A177C, the missense mutant of lacY gene. (iii) Flow chart showing the present minicircle production protocol. (c) Stepwise genetic modification of the bacterial genome to make the current ZYCY10P3S2T strain.
Figure 13:
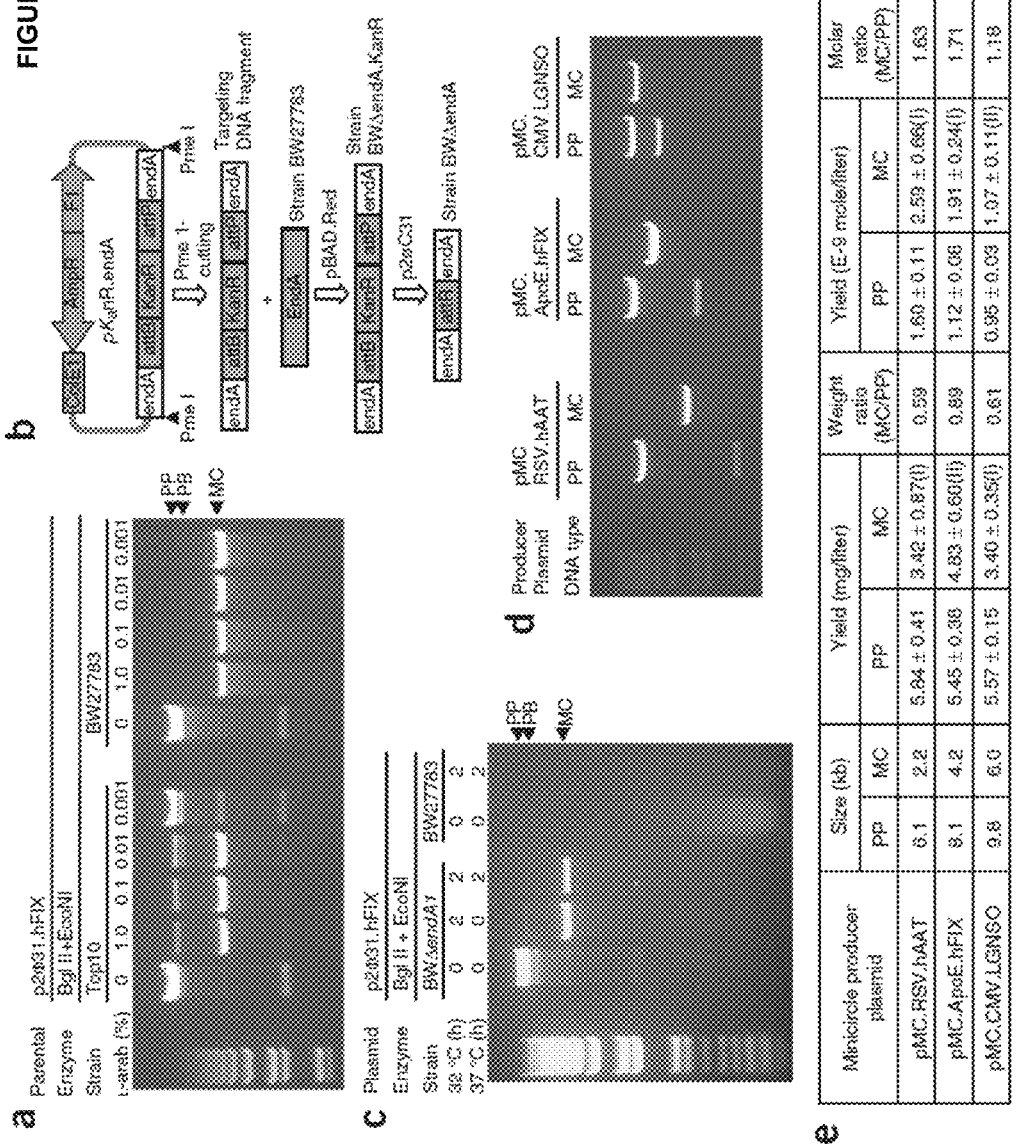
FIG. 13 Improvement in minicircle quality and quantity. (a) Strain BW27783 produced minicircle (MC) with enhanced purity. Minicircles were produced according to the protocol described previously$_6$. 2φ31.hFIX, minicircle producer plasmid (PP); BglII+EcoN1, two restriction enzymes used to cleave MC before electrophoresis; $_{I}$-arab(%), percent of $_{I}$-arabinose in the minicircle induction reaction; PB, plasmid backbone circle. (b) Strategy for inactivation of endA. pK$_a$nR.endA, the plasmid used to generate the Pme1-restricted targeting DNA fragment; KanR, kanamycin-resistance gene; attB and attP, the bacterial and phage attachment sites of bacteriophage φC31 integrase; boxed endA, PCR-generated 329- and 754-bp end A fragments; pBAD.Red, a plasmid expressing the bacteriophage λ homology recombination complex (Red) under the control of araC.BAD (BAD); p2φC31, a complementing plasmid encoding two copies of BAD.φC31 gene, one copy of BAD.I-SceI gene and one I-SceI site; BWΔendA, a strain derived from BW27783 with the endA interrupted. (c) Minicircle DNA integrity before and after disruption of the endA gene. Before disrupting endA, we observed repeatedly large variations in the degree of plasmid degradation as shown in a and c. Because the endonuclease A is a membrane-bound enzyme, it was possible that its membrane release and activation varied during plasmid preparation. 32° C. and 37° C., the incubation temperature. All reactions contained 1% $_{I}$-arabinose. (d) Quality of the minicircle determined by gel analyses. Minicircle was made according to the simplified protocol outlined in FIG. 1b; DNAs were cleaved before electrophoresis. (e) Yield of minicircle producer plasmids and minicircle vector DNAs. The yield was derived from triplicate 400-ml overnight cultures; PP, minicircle producer plasmid; MC, minicircle. Wilcoxon rank sum test comparing the yield of minicircle and its minicircle producer plasmid: (I), P<0.05; (II), P>0.05. We used the following formula to convert the yield from mg/l to mol/l: mol/l=[yield (mg/l)×10E−3 g/l]/[size (kb)×1,000×330×2 g/mol], where 330 is the average molecular weight of dNTP. The minicircle producer plasmid, pMC.RSV.hAAT is schematically illustrated in FIG. 6d.
Figure 14:
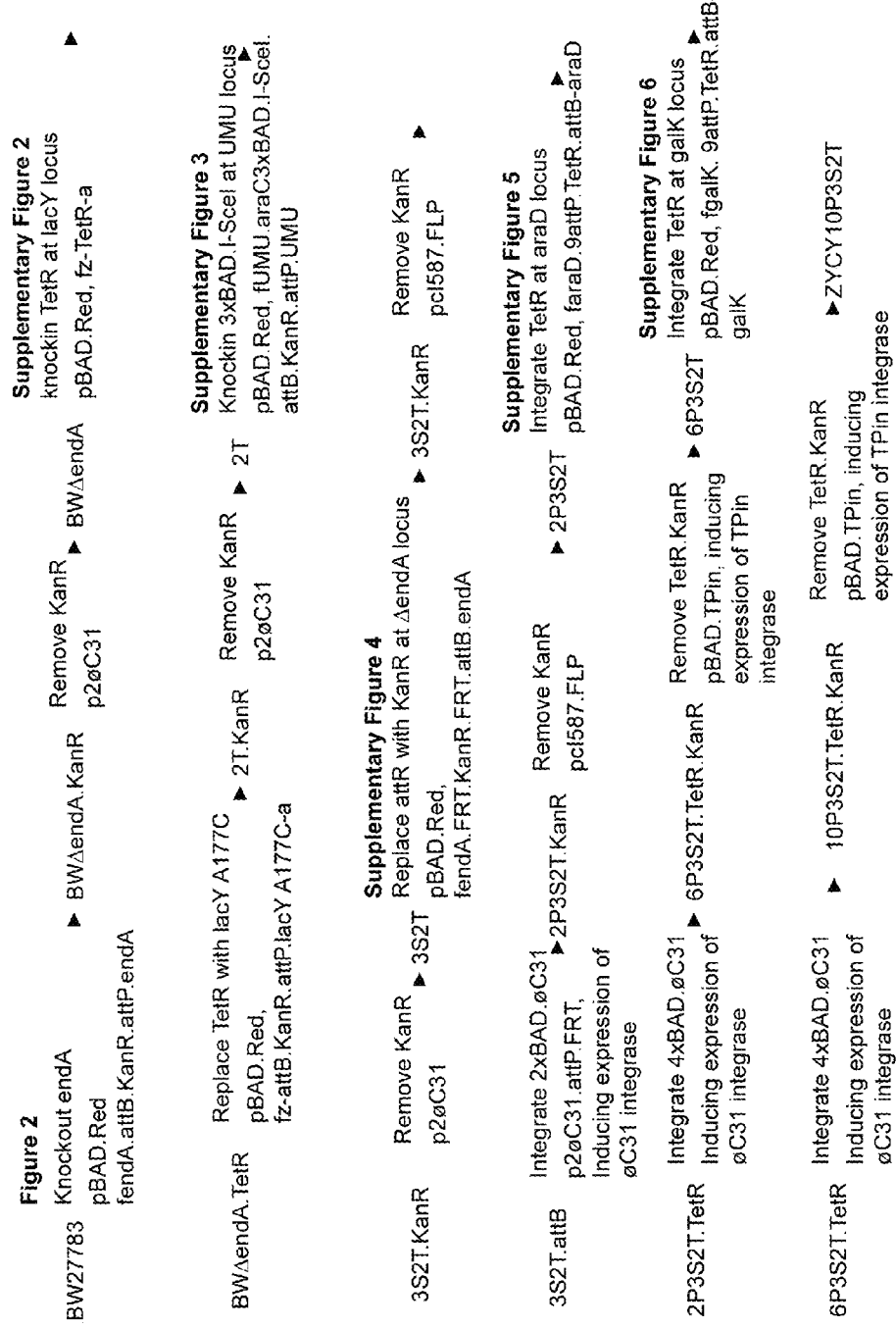
FIG. 14. A flowchart summarizing the stepwise genetic manipulation of the bacterial genome. The bacterial strains are boxed.
Figure 15:
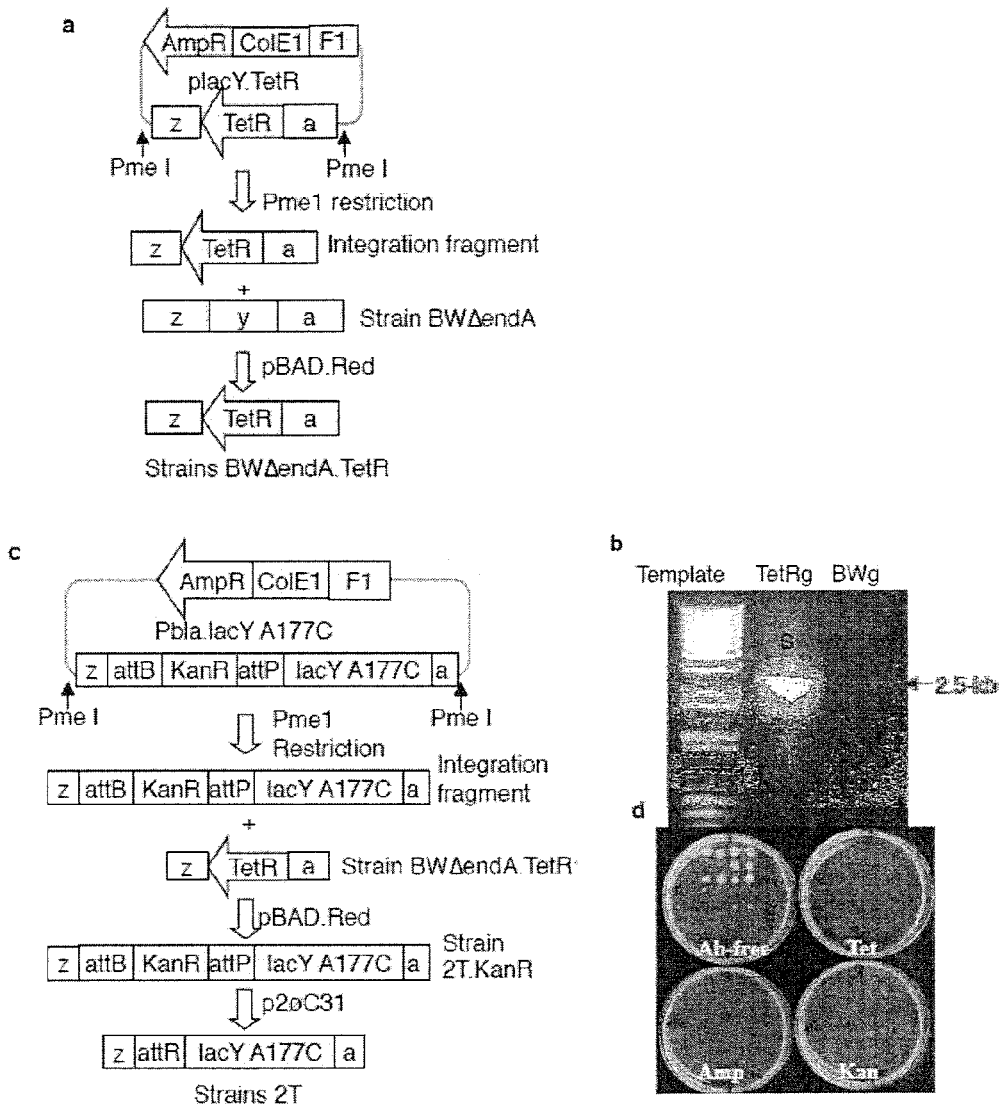
FIG. 15A-D. Integration of 2nd L-arabinose transporter mutant lacY A177C. (a) Flow chart illustrating procedure for preparing target site. placY.TetR, the plasmid used to prepare the Pme1-restricted integrating fragment; z, y and a, the structural genes of lactose operon; the boxed z and a, PCR-generated 425- and 227-bp of z- and a-specific sequences. (b) PCR illustration of integrant. 2.5-kb, integrant-specific PCR product; TetRg, genome of strain BWΔendA.TetR; BWg, genome of BW27783. (c) Mutant lacY A177C knock-in strategy. pbla.lacY A177C, the plasmid for producing the Pme1-restricted integrated DNA fragment; bla, the beta-galactosidase gene promoter. (d) Selection of the strain 2T. Colonies that lost all three antibiotic resistance phenotypes were selected using the 4 agar plates containing different antibiotics. Ab-free, antibiotic-free; Tet, tetracycline (12 μg/ml); Amp, ampicillin (25 μg/ml); Kan, kanamycin (25 μg/ml).
Figure 16:
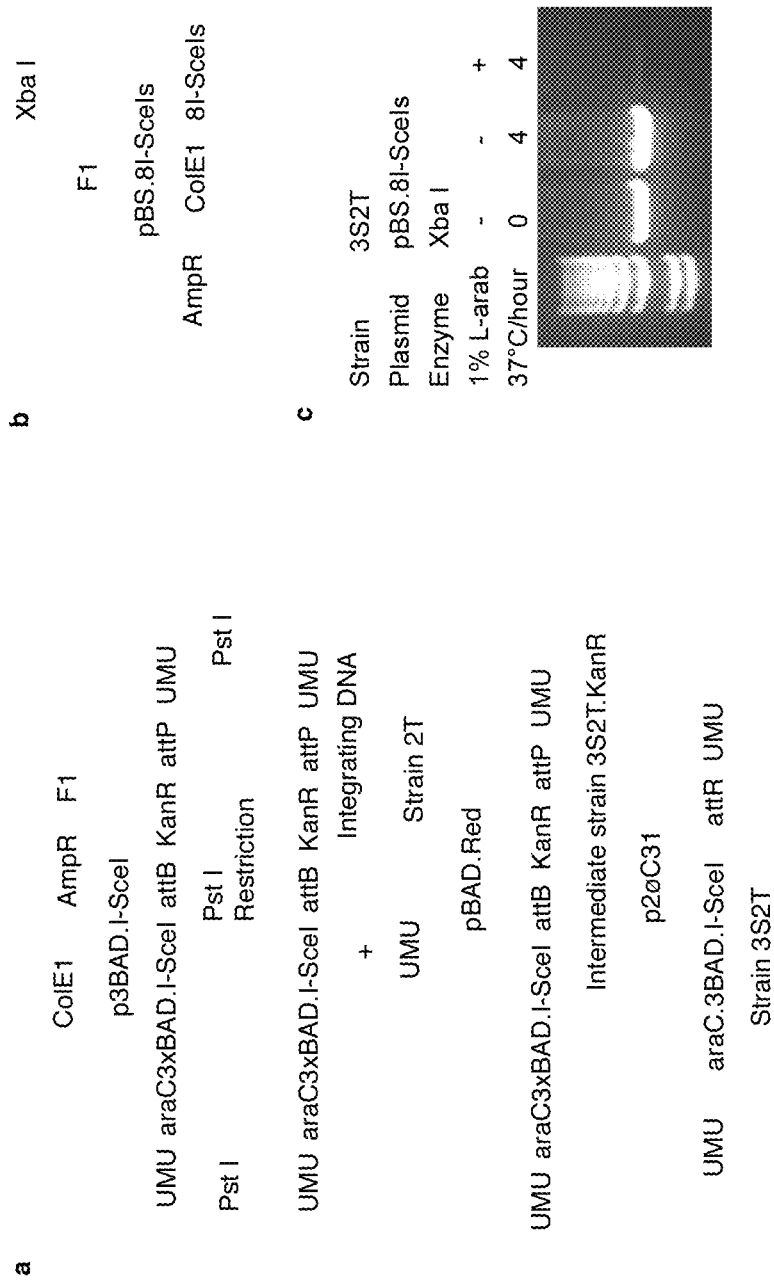
FIG. 16A-C. Integration of BAD.I-SceI gene. (a) Flow chart showing the BAD.I-SceI gene knock-in procedure. p3BAD.I-SceI, the plasmid encoding 3 tandem copies of the I-SceI gene under the control of BAD (BAD.I-SceI); UMU, the UMU D gene; the boxed UMU, PCR-generated 737- and 647-bp UMU-specific product, respectively; araC, the repressor gene of araC.BDA system; integrating DNA, the DNA fragment derived from p3BAD.I-SceI via Pst 1 restriction; strain 2T, the *E. coli* expressing 2 constitutive L-arabinose transporters cp8.araE and bla.lacY A177C (FIG. 4); strain 3S2T, generated by Red mediated integration of the above integrating fragment to the UMU gene of strain 2T. (b) pBS.8I-SceIs, a pBlueScript base plasmid encoding 8 tandem copies of the I-SceI site. (c) Demonstration of function of the integrated I-SceI gene in strain 3S2T. An overnight culture of the 3S2Tstrain transformed with pBS.8I-SceIs was re-suspended in LB with or without 1% L-arabinose and incubated at 37° for 4 hours; Xba I, the restriction enzyme used to cut the plasmid before electrophoresis.
Figure 17:
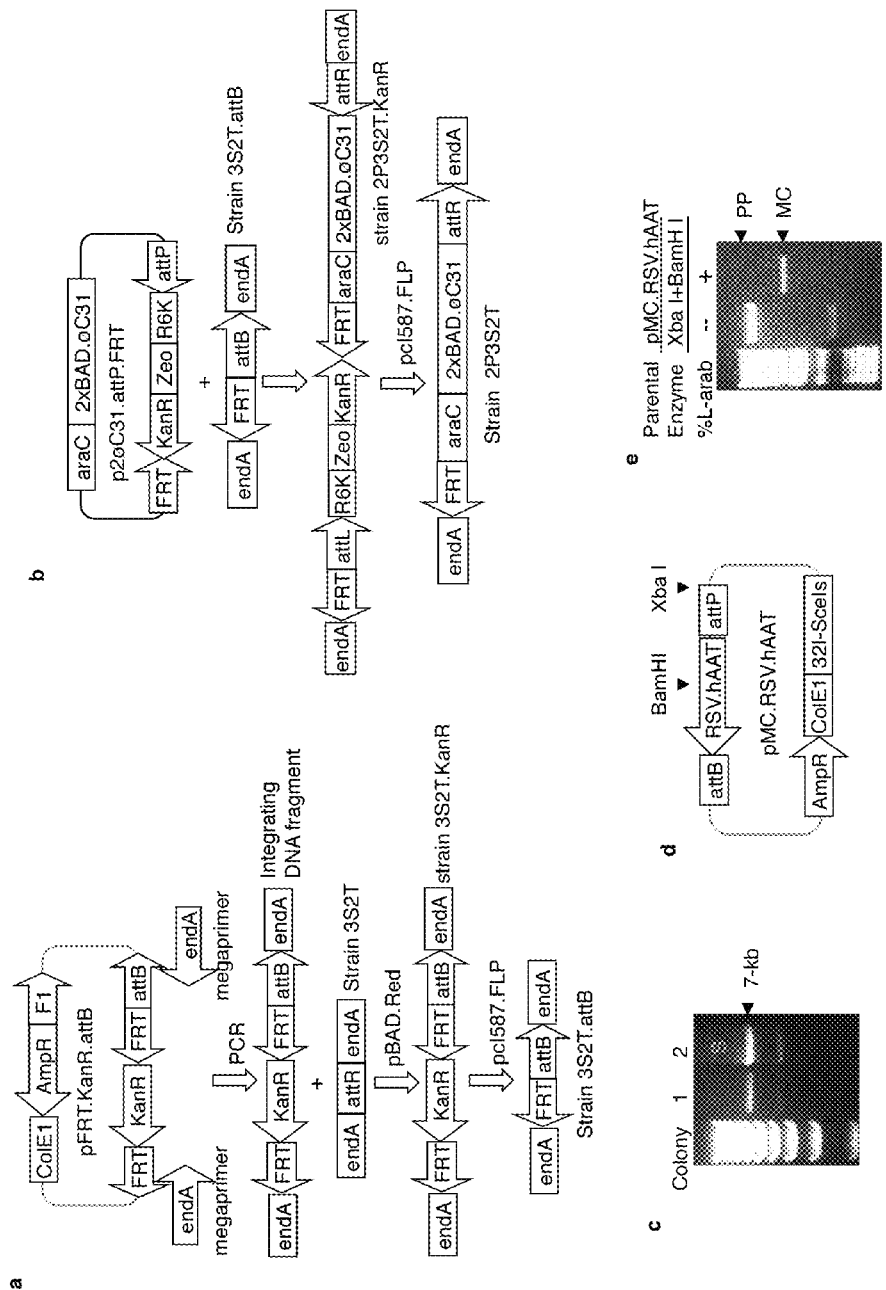
FIG. 17A-E. Integration of 2 copies of BAD.øC31 gene. (a) Preparation of genomic target site. pFRT.KanR.attB, the plasmid serving as PCR template; FRT, the binding site of flipase (FLP); megaprimers, 329- and 754-bp of endA sequences, generated by PCR, to serve as PCR primers for generating the integrating DNA fragment; the PCR product was integrated into the modified endA site of strain 3S2T via Red-mediated reaction; subsequently, the KanR was eliminated via FLP-mediated reaction between the two flanking FRTs, resulting in the strain 3S2T.attB; cI587, the bacteriophage Lambda temperature sensitive promoter. (b) Integration of BAD.øC31. p2øC31.attP.FRT, a conditional replicating plasmid carrying R6K origin capable of supporting plasmid replication only in the cell expressing the pir protein; Zeo, zeocin. (c) PCR illustration of the integrant. 7-kb, the size of the PCR product generated by a pair of endA-specific primers. S, partial DNA sequencing of the DNA in the band. (d) The minicircle producer plasmid pMC.RSV.HAAT. R, the Rous Sarcoma virus long terminal repeat (promoter); H, human alpha-1 antitrypsin cDNA; B, bovine growth hormone gene polyadenylation signal; 32I-SceIs, 32 consecutive I-SceI cutting sites. (e) Illustration of genomic øC31 integrase function. The minicircle was made according to the protocol described previously. Xba I+BamHI, 2 restriction enzymes used to cut the DNA before electrophoresis.
Figure 18:
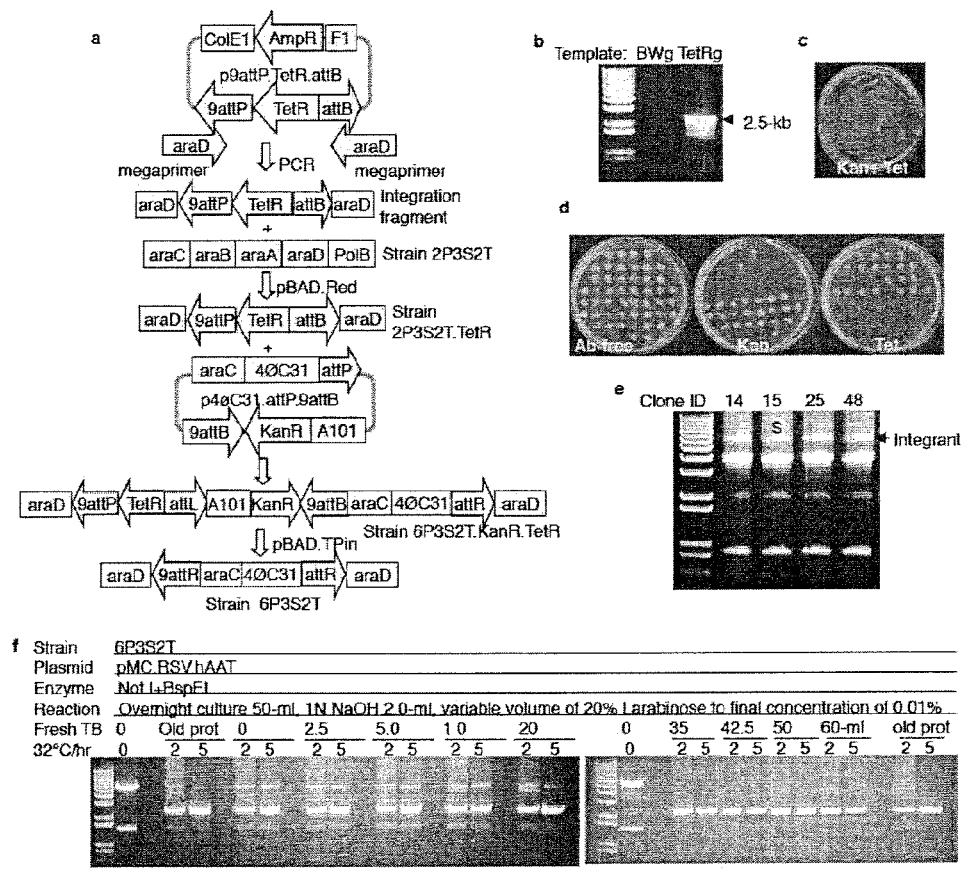
FIG. 18A-F. Integration of 4 copies of BAD.øC31. (a) Flow chart illustrating the integration procedure. p9attP.TetR.attB, the plasmid served as template for PCR-generation of the integrating DNA fragment; 9attB and 9attP, the bacterial and phage attachment sites of the bacteriophage TP901-1 integrase (TPin); the boxed araD, PCR-generated 275- and 310-bp araD specific product, respectively; p4øC31.attP.9attB and pBAD.TPin, two complementing plasmids carrying the temperature-sensitive A101 origin of replication; 9attR, the recombination product between 9attB and 9attP. (b) PCR illustration of the altered araD locus. 2.5-kb, size of the PCR product generated by a TetR- and an araD-specific primers. (c) Selection of strain 6P3S2T.KanR.TetR. Kan+Tet, the plate containing both Kan and Tet. (d) Elimination of KanR and TetR., marked colonies that lost both KanR and TetR are circled. (e) PCR illustration of integrant. Integrant, PCR product generated by a pair of araD-specific primers. (f) Optimizing minicircle production procedure. Reaction, minicircle formation reaction each comprised a 50-ml overnight culture, 2-ml 1N sodium hydroxide, indicated volume of fresh TB and L-arabinose to a final concentration of 0.01%; old prot, previous protocol for minicircle production.
Figure 19:
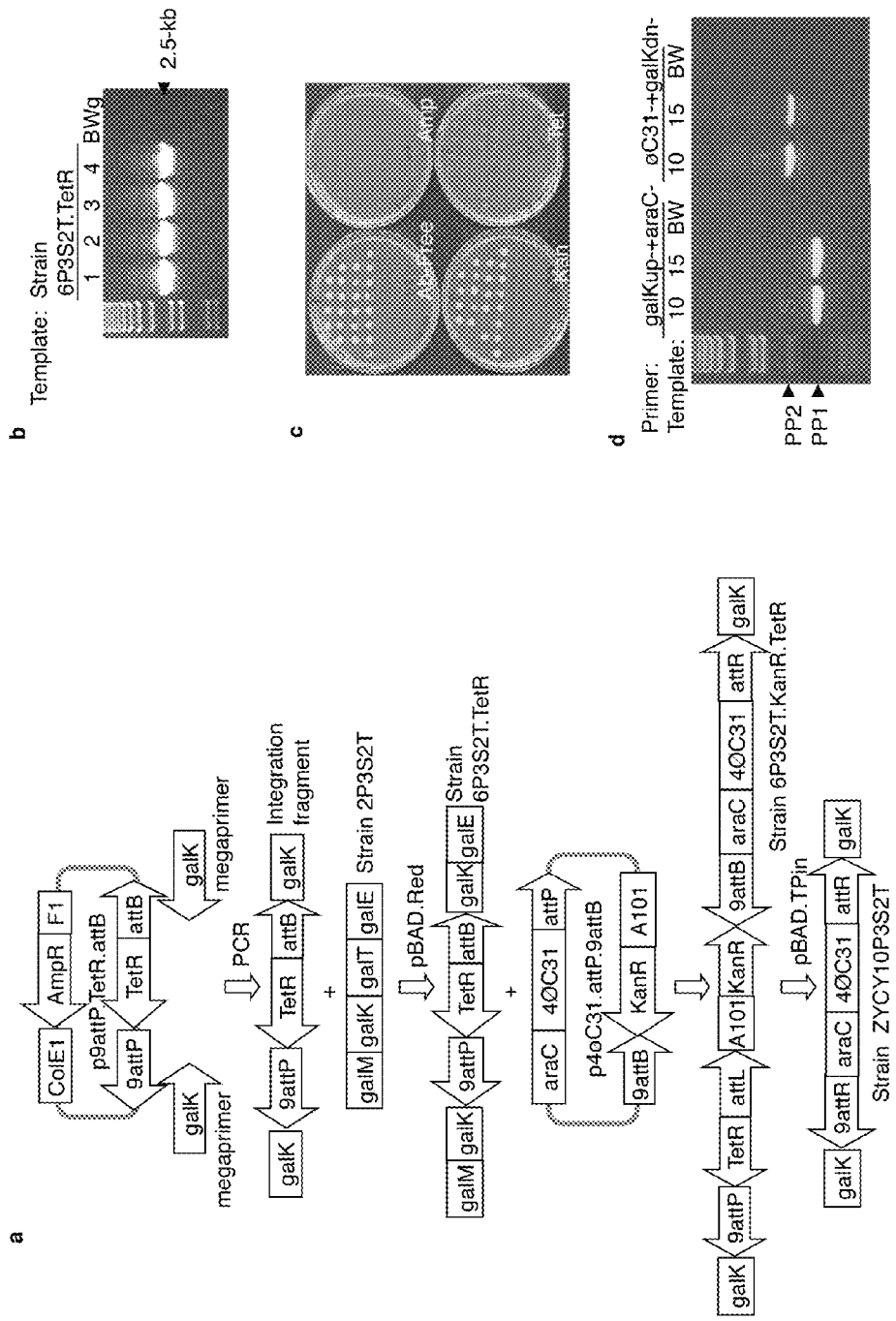
FIG. 19A-D. Integration of the 7''' to 10''' copies of BAD.sC31. (a) The integration procedure was the same as that for integration of the 3rd to 6th copies of the BAD.oC31 cassette (FIG. 7a); galK, galactokinase gene. (b) PCR reaction to confirm the prepared target. 2.5-kb, the expected size of the PCR product generated by a TetR- and a galK-specific primers. (c) Screening of strain ZYCY 1 OP3S2T; the AmpR-IKanR-ITetR-colonies are circled. (d) PCR illustration of the integrant elements; galKup, the up-stream galK-specific primer; galKdn, the downstream galK-specific primer.

Subsequently, we used BWΔendA stain to prepare minicircle with p2øC31.hFIX (FIG. 1, panel A) and found that the minicircle was intact (FIG. 3, panel C). Surprisingly, we observed trace amount of the impurity DNAs in the minicircle preparation that were not seen in minicircle generated using the parental strain BW27783 (FIG. 2, panel A). We hypothesized that the trace amount of impurity DNA was derived from dead bacteria; alternatively, they were resulted from the incomplete elimination of the "all-or-non" behavior as suggested by Morgan-Kiss and colleagues (PNAS 99:7373, 2002). These authors found that the lactose transporter mutant LacY A177C gains additional function to work as L-arabinose transporter and expressing this mutant is able to completely eliminate the "all-or-none" phenomenon. Therefore, we obtained the mutant LacY A177C gene from Dr. Cronan J E of Yale University, placed it under the control the constitutive promoter of lactosidase gene (bla) and used it to replace the wild type LacY gene in the genome of an intermediate strain (FIG. 7, panel B; FIG. 9, panels A to D).

Example 3

Expressing ISce I Gene from Bacterial Genome

We hypothesized that the best way to prepare minicircle free of øC31- and ISce I-encoding DNA is to express both the recombinase øC31 and restriction enzyme ISce 1 from the bacterial genome. We hypothesized that dead bacteria occur in any culture so that contamination is inevitable, and that these impurity DNAs cause more harm because they are circular, stable, and physically indistinguishable from the minicircle and hence hard to be removed. In contrast, when øC31 and ISce I are integrated into the bacterial genome, these risky genes, as linear DNA of bacterial genome debris, have less chance to contaminate, are more easily removed, and, degradable by host exonucleases, causing little or no harm to the recipient. Therefore, we set forth to relocate the BAD.ISce I cassette from the minicircle producing plasmid to the bacterial genome.

Figure 4:
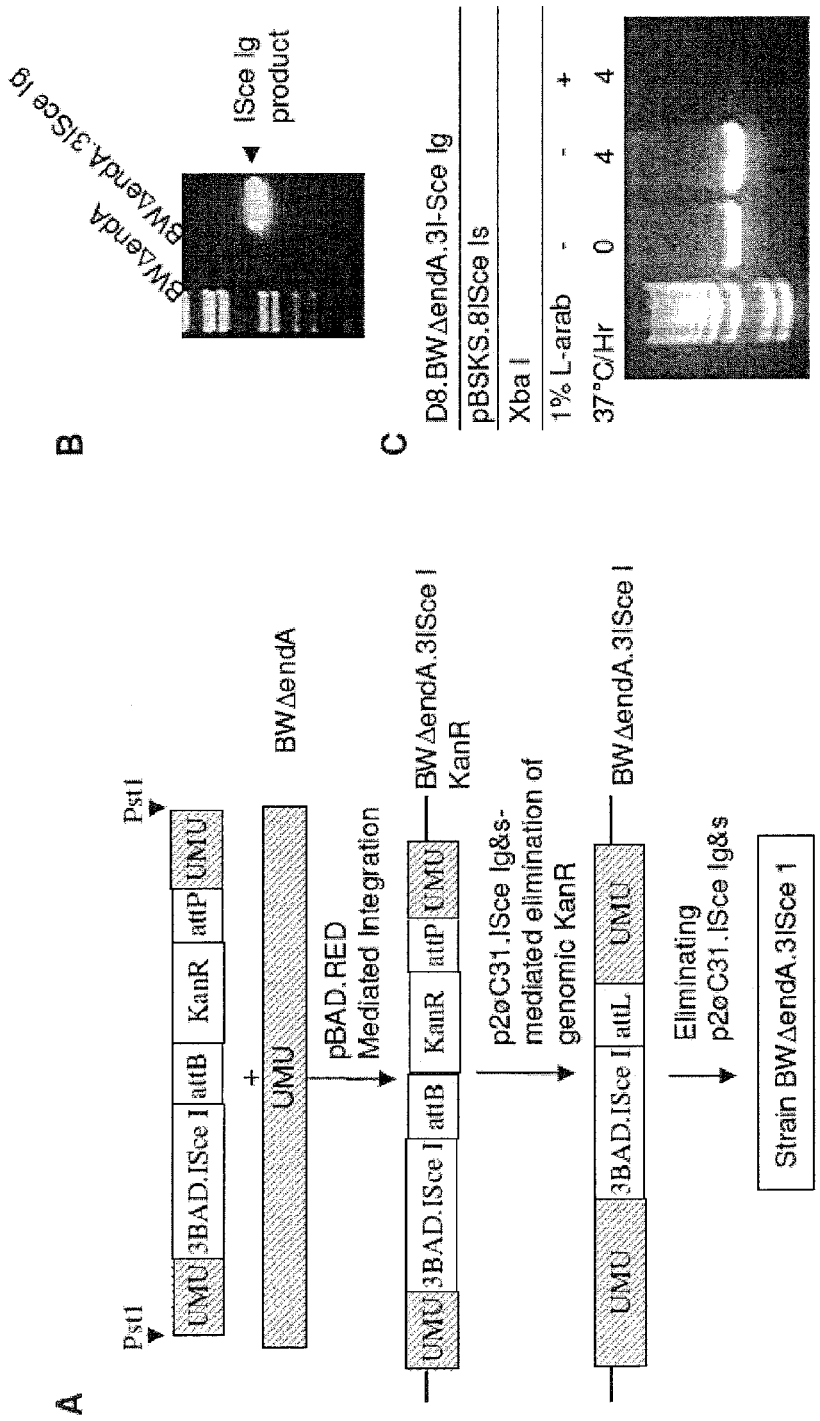
FIGS. 4A-4C show integration of BAD.ISce I gene. Panel A shows a flow chart of DNA integration. The linear targeting DNA, which comprised 3 tandem copies of the BDA.ISce I cassette and one kanamycin cassette and two flanking UMU targeting sequences, was prepared from plasmid p3BAD.ISce I.KanR.UMU (FIG. 1, panel F) via Pst1 digestion; we integrated it into UMU locus of strain BWΔendA following the same procedure (Datsenko and Wanner B L, PNAS 97:6640, 2000) as described in the legend of FIG. 3; at the end, the new strain BWΔendA.3ISce I was obtained. Panel B shows PCR illustration of integrated ISce I gene. Likewise the integration of the ISce I gene was confirmed by generating the expected PCR product using ISce 1-gene-specific primers in strain BWΔendA.3ISce 1, but not in the precursor BWΔendA. Panel C shows an illustration of ISce I activity. The strain BWΔendA.3ISce I was transformed with plasmid p8ISce Is (FIG. 1, panel G) carrying eight consecutive ISce I restriction sites. The transformed bacteria were resuspended from overnight culture in fresh LB with or without 1% L-arabinose and incubated at 37° C. for 4 hours; an aliquot without any treatment was used as control. Plasmid DNA was isolated, linearized with Xba I, and analyzed in agarose gel. The DNA bands from two cultures free of L-arabinose were evident and almost equal, but barely visible from the culture expressing ISce I enzyme, indicating that the integrated ISce I genes were working.
Figure 5:
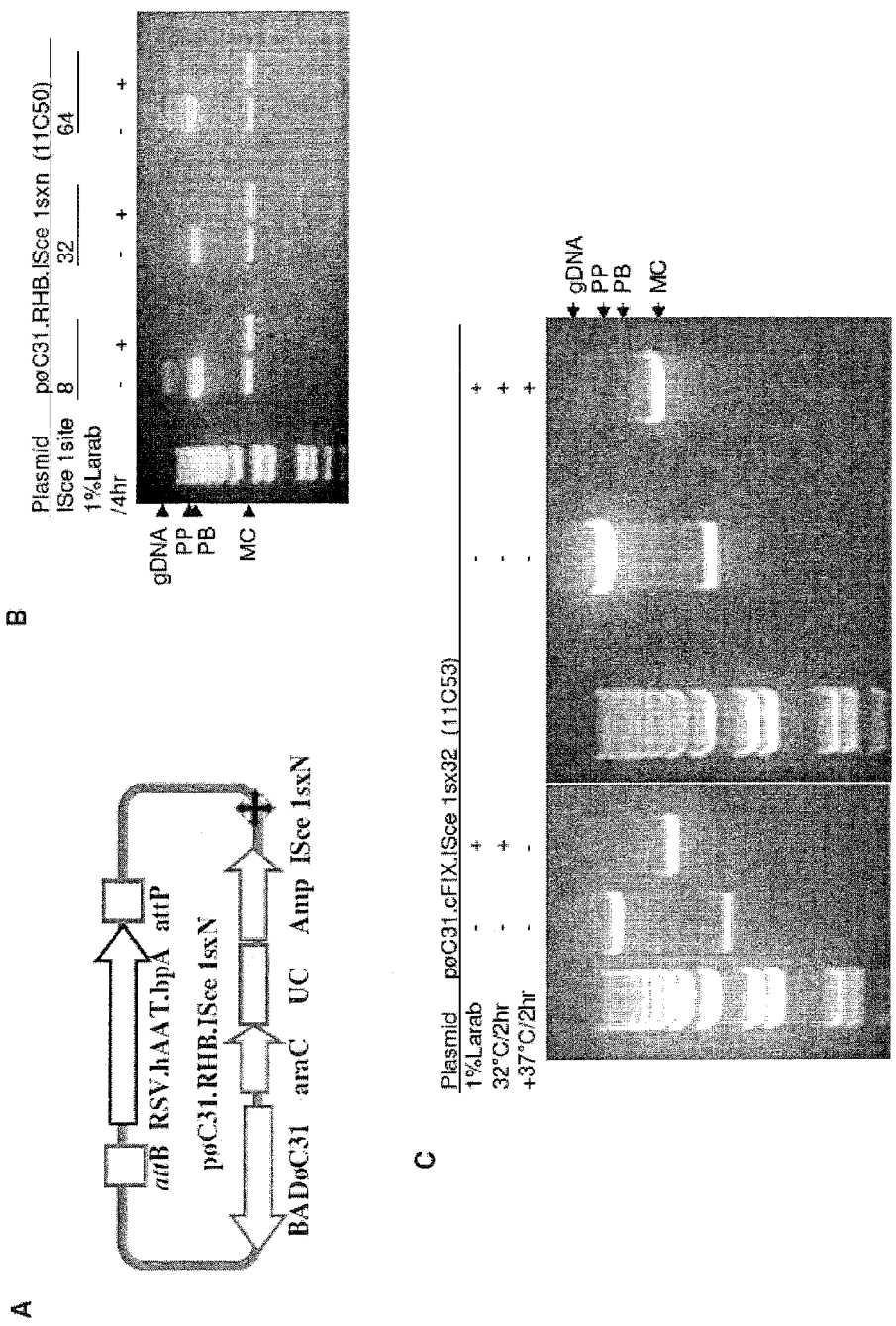
FIGS. 5A-5C show production of minicircle formulations using bacteria having inactive endA gene and integrated BAD.ISce 1 gene. Panel A shows parental plasmid construct used to produce the minicircle vectors. The plasmid includes one copy of the BDA.øC31 recombinase gene with multiple ISce 1 restriction sites (N=8, 32 or 64). Panel B shows an estimated amount of contaminating nucleic acids in the three minicircle preparations (MC=minicircle, PP=parental plasmid, PB=plasmid backbone, gDNA=genomic DNA) that were cultured in the presence (+) or absence of (−) of 1% L-arabinose for 4 hours. The minicircles were generated from the plasmid described in Panel A and the DNA preps were digested with Spe 1 and Xba 1, which cut once through the minicircle or the plasmid backbone (BB), respectively. Panel C shows a determination of the quality of the minicircle preparation at varying temperatures. The DNA was cut with Xba 1, which cut once through both the minicircle (MC) and plasmid BB (PB) simultaneously.

To do this, we made the plasmid p3BAD.ISCe Ig.Kan-R.UMU carrying 3 tandem copies of the BAD.ISce 1 cassette and two PCR-generated sequences targeting the bacterial UMU locus flanking the 3BAD.ISce 1.attB-kanR-attP cassettes (FIG. 1, panel F). Following the same protocol inactivating the endA gene as described above, we successfully integrated the ISce 1 genes into the BWΔendA genome and obtained the strain BWΔendA.3ISce 1 (FIG. 4, panel A). Likewise, we detected the ISce 1 gene via PCR using the gene-specific primers (FIG. 4B). To determine if the integrated ISce I gene was functioning, we transfected the new bacterial strain with plasmid p8ISce 1s carrying 8 consecutive ISce I restriction sites (FIG. 1, panel G) and found that the plasmid was almost completely lost when ISce 1 enzyme was induced to express for 4 hours, but remained intact when expression of ISce I was absent (FIG. 4, panel C). We found that the genomic ISce 1 gene worked as well in the minicircle producing settings and this will be described in more details below (FIG. 5, panels B and C).

Example 4

Function of Genomic ISce 1 Gene in Minicircle Preparation Settings

In the previous section, we demonstrated that the three copies of the integrated BAD.ISce 1 gene were functioning by showing the destruction of plasmids carrying 8-ISce 1 restriction sites. Here, we provide further evidence showing that the new strain worked well in eliminating the impurity DNA in actual minicircle preparation setting. We conducted two experiments making minicircle using the new strain. In the first experiment, we used three parental plasmids which contained a 2.3-kb RSV.hAAT.bpA cassette and one copy of the BAD.øC31 gene each and 8- or 32- or 64-consecutive ISce 1 sites, respectively (FIG. 5, panel A). We transformed the strain BWΔendA.3ISce 1 with the plasmids and prepared minicircle using routine protocol as described earlier (Chen et al., Hum Gene Ther 16:126, 2005). We estimated the amount of the impurity DNA by agarose gel electrophoresis using the restricted minicircle preps and found that the impurity was barely visible in the three minicircle preps (FIG. 5, panel B). In the second experiment, we used a similar minicircle producing plasmid encoding a 4.2-kb expression cassette with 32-ISce 1 sites in the plasmid backbone and found that the contaminant DNA was almost invisible (FIG. 5, panel C). Therefore, the integrated ISce 1 gene, in concert with multiplying its sites, worked very well.

Example 5

Integration of Multiple Copies of øC31 Gene into the Genome of BWΔendA.3ISce Ig

Due to their potential in damaging the recipient genome, complete elimination of the øC31 and ISce 1 genes from minicircle prep is an important safety criterion of clinical grade vector DNA. To achieve this, we further relocated the øC31 gene from plasmid bacterial backbone sequences to the bacterial genome after integrating 3 copies of the ISceI gene. It is expected that contamination of both øC31 and ISce 1 genes in the minicircle prep will be encoded only by linear bacterial genomic DNA debris; which is physically distinguishable from the minicircle. In particular, the linear DNA can be more easily eliminated by multiple commercially available biological or chemical or physiological means. For example, lambda exonuclease can be used to chew up the linear DNA without damaging the minicircle DNA preparation, resulting in minicircle product free of both øC31 and ISce 1 genes.

Three copies of the BAD.ISce 1 cassette have been integrated into the bacterial genome and have been found to be functioning properly (FIG. 5, panels B and C). We have conducted an experiment integrating 6 copies of the BAD.øC31 to the genome of the strain BWΔendA.3ISce 1. FIG. 7, panel B shows the final version of the bacterial genome with all the genetic alterations we have made and will make; which strain will allow preparation of clinical grade minicircle vectors, free of øC31 and ISce 1 coding sequences.

Figure 8:
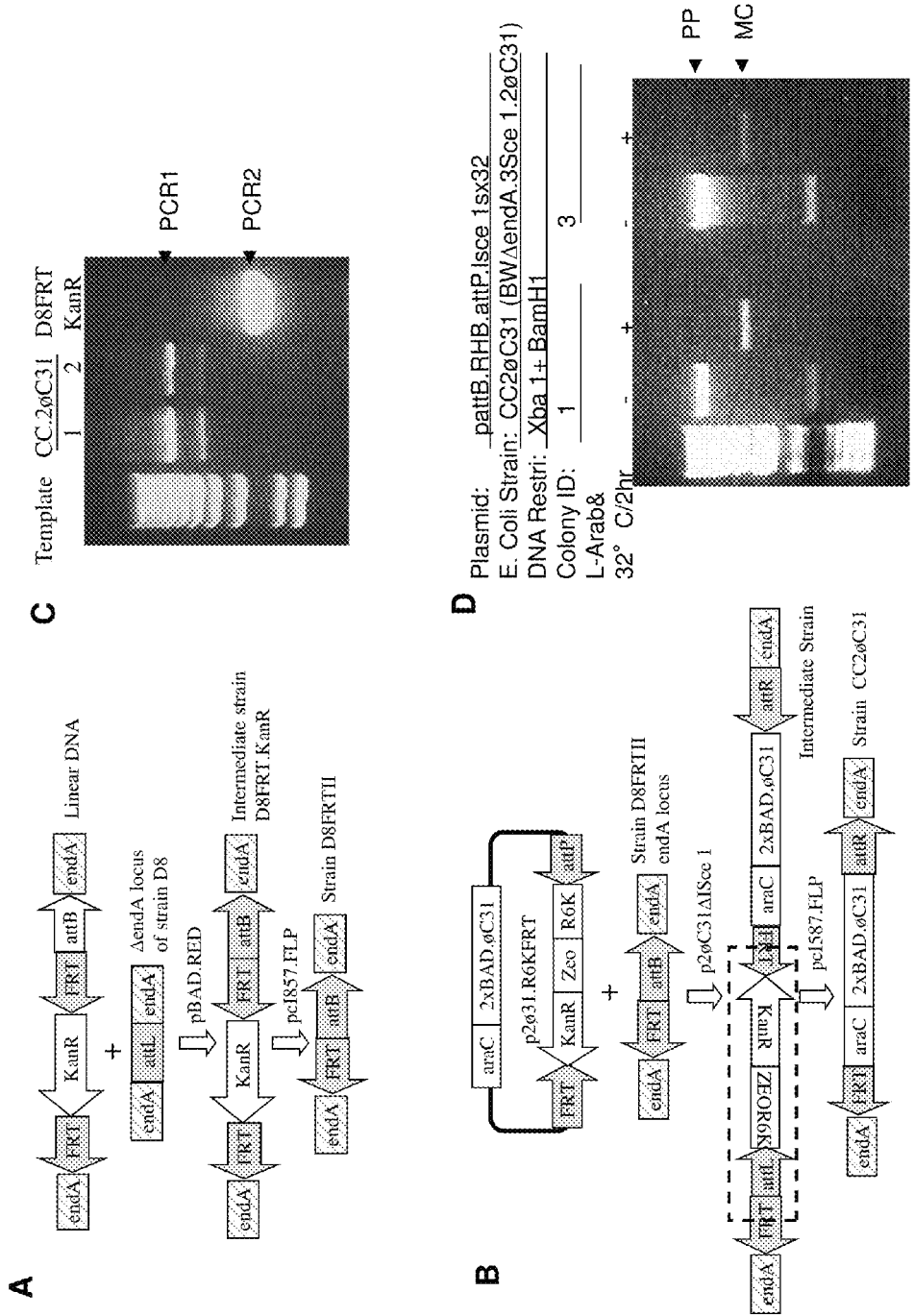
FIGS. 8A-8D. Genomic integration of the BAD.øC31 gene.

FIGS. 8A-8C demonstrate integration of BAD.øC31 gene. Panel A shows integration of targeting attB site in the ΔendA locus of strain D8 (BWΔendA.3ISce 1) made earlier (FIGS. 3 & 4). We prepared the linear DNA carrying an attB sequence from a precursor plasmid digested with Pme 1; we integrated it into the ΔendA locus mediated by the RED enzymes as described earlier (FIG. 3A). Subsequently, we eliminated the KanR gene from the integrant via the recombination between the two FRT sequences mediated by flipase expressed from plasmid pcI857.FLP; we incubated the bacteria at 43° C. for 8 hours to induce the expression of flipase and killed the plasmid at the same time. Consequently, we obtained the strain D8FRTII carrying a modified ΔendA locus comprising a FRT and an attB sites. Panel B shows the integration of 2 copies of the BAD.øC31 gene. We transfected the strain D8FRTII with plasmid p2øC31 and induced expression of the øC31 enzyme to mediate the integration of the subsequently transfected plasmid p2øC31.R6KFRT into the endA locus via recombination between the attB and attP; we killed the plasmid p2øC31 via restriction digestion with ISce 1 expressed from the genomic endonuclease gene; we then removed the R6K.KanR sequences from the integrant via the recombination between the two FRT sites as described above (FIG. 8A). We used the DNA origin R6K in the integrating plasmid, for R6K requires protein pi to function and is capable of supporting plasmid replication only in the pi-expressing strains such as PIR1 (Invitrogen, Carlsbad Calif.), but not in the pi-negative D8FRTII; this feature ensures the selection of only the colonies carrying the integrated, but not the episomal, antibiotic resistance gene (KanR) encoded in the plasmid p2øC31.R6KFRT. Panel C demonstrates PCR evidence of the integrant.

PCR reactions were conducted using a primer pair immediate outside the endA locus; lanes 1 and 2 were the PCR reactions using the genomic DNA of clones 1 and 3 of CC2øC31 strain as templates, while lane 3 the strain D8FRTII; PCR 1 (7.5-kb) and 2 (2.5-KB) are the expected products from respective reactions. Panel D shows the formation of minicircle (MC, about 2.5-kb) by strain CC2øC31 clones 1 and 3. The parental plasmid pattB.RHB.attP.ISce 1sx32 encodes a same RHB transgene and 32 ISce 1 sites as the parental plasmid described in FIG. 5A, but contains no BAD.øC31 gene. The minicircle was produced using the standard protocol as described previously (Chen et al., Humn Gene Ther 16:126, 2005); the DNA was restricted with Xba I plus BamH1 before electrophoresis.

Example 6

Our efforts to optimize minicircle production led us to develop an improved bacterial genome modification strategy. The enhancements include: (i) the use of a circular integrating plasmid instead of linear DNA, allowing repeated integration of the same or different DNA sequences of up to 50 kb in selected targets; (ii) inclusion of a second recombinase, allowing selective removal of unwanted sequences, such as the hybrid sequences responsible for the reverse recombinase reaction, along with the useless or harmful plasmid backbone DNAs, from the genome; and (iii) the use of the TPin/9attB.9attP recombination system, eliminating the inherent problems with the FLP/FRT system, in which the uncontrolled reaction between the substrate and product FRTs makes repeated integration virtually impossible. These bacterial gene modifications would be difficult to achieve with conventional homologous recombination methods. In our approach we were able to remove one of the two recombination hybrids (either attL or attR), disabling the reverse reaction and resulting in a stable genomic insertion. Recent studies have shown that repeated gene sequences inserted into the bacterial genome are stable for at least 80 generations. This type of site-specific integration broadens the ability to make stable genetic modifications in prokaryotic and eukaryotic genomes.

Integration of the BAD.φC31 cassettes. Three experiments were conducted to integrate ten copies of BAD.φC31 into the bacterial genome: two, four and four copies into the ΔendA locus, araD gene and galK gene, respectively. All three integration events were achieved by φC31 integrase-mediated, site-specific recombination between the attB or attP site in an integrating plasmid, and the attB or attP in the targeted genomic sites as described for the endA gene disruption.

In an earlier attempt, we found that the integrated BAD.φC31 was lost soon after its integration. This is probably the result of a reverse reaction mediated by an uncharacterized excisionase or cofactor that worked in concert with φC31 integrase produced by the leaky expression from the integrated BAD.φC31. To stabilize the integrant, we designed a double recombination strategy. The φC31 integrase was used to mediate an integration event followed by FLP- or TPin-mediated recombination to remove the attL. This would eliminate the possibility of a reverse reaction between the attL and attR. For integration of the 2BAD.φC31, we used the Red-mediated homologous recombination strategy with a linear DNA containing an attB site, a KanR gene and two flanking FRTs for insertion into the ΔendA locus. To remove the KanR, cells from one 3S2T.KanR colony were transformed with pcI587.FLP, and cells from a transformed colony were grown in 5 ml of antibiotic-free LB at 42° C. for 8 h. This induced the expression of FLP to mediate the recombination between the two FRTs, resulting in the elimination of KanR followed by the loss of the temperature-sensitive pcI587.FLP. Subsequently, the cells named 3S2T.attB were transformed with p2φC31.attP.FRT. Cells from one transformed colony were grown in 2-ml of LB containing 1% l-arabinose at 32° C. for 2 h, which induced the expression of φC31 integrase to mediate the recombination between the attB in the ΔendA locus and the attP in the plasmid. The same FLP-mediated FRT-FRT recombination was conducted to mediate the removal of the attL and R6K.Zeo and KanR, resulting in the strain of 2P3S2T. The integrated 2BAD.φC31 was confirmed by DNA sequencing of the locus-specific PCR product (FIG. 6c) and by demonstrating the function in mediating minicircle formation. Integration of the four copies of the BAD.φC31 gene into the araD and galK loci, respectively, was also mediated by φC31 integrase; however, the removal of the attL was mediated by bacteriophage TP901-1 integrase (TPin). To do this, we used the Red recombination system to integrate a DNA fragment encoding TetR flanked with an attB and a phage attachment site of TPin (9attP) into the araD or galK site and confirmed the integrant by DNA sequencing of the integrant-specific PCR product. We integrated p4φC31.attP.9attB into the modified araD or galK locus following the same procedure as used for integrating the p2φC31.attP.FRT with modifications. We selected the colonies with integrants using plates containing both Tet and Kan, transformed the selected intermediates 6P3S2T.KanR.TetR or 10P3S2T.KanR.TetR with plasmid pBAD.TPin, and screened the resulting colonies using triple antibiotic resistance (Tet, Kan and Amp). We grew the cells from one colony in 2 ml of antibiotic-free LB containing 1% l-arabinose, with shaking (250 r.p.m.) at 43° C. for 6-8 h before spreading onto an antibiotic-free plate and incubated at 43° C. overnight. l-arabinose induced expression of both recombinases, however, the incubation temperature allowed significant TPin integrase activity but little φC31 integrase activity, resulting in the TPin integrase-mediated removal of attL and selection of colonies with the desired integrant, 6P3S2T and ZYCY10P3S2T.

Constructs. Plasmid pKnR.endA was made by inserting the following DNA elements: the kanamycin-resistance gene (KanR) flanked by the bacterial (attB) and phage (attP) attachment sites of the *Streptomyces* bacteriophage φC31 integrase and PCR-generated 329- and 734-bp fragments of endonuclease A gene (endA) into the pBlueScript (Stratagene) plasmid. The plasmid p2φC31 was made by removing the human factor IX (hFIX) transgene and flanking attB and attP sites from p2φC31.hFIX$_6$, the BAD.I-SceI cassette and I-SceI site were retained. To make the plasmid p3BAD.I-SceI, the araC repressor gene together with three tandem copies of BAD.I-SceI gene were inserted downstream of the attB site of the plasmid pK$_a$nR.endA (FIG. 2b), followed by replacement of endA with the 737- and 647-bp UMU fragment generated by PCR. The plasmid pBS.8I-SceIs was constructed by inserting eight consecutive copies of the 18-bp I-SceI site into pBlueScript. The plasmids pBAD.Red and pcI587.FLP, which both carry the temperature-sensitive A101 origin of replication, were obtained from the *E. coli* Genetic Resource Center of Yale University. Plasmid pFRT-.KanR.attB was generated by inserting the attB site and the KanR flanked with FRT sites of flipase into pBlueScript using DNA oligonucleotides. Plasmid p2φC31.attP.FRT was constructed using our previous minicircle-producing plasmid p2φC31.hFIX$_6$ as starting material. The sApoE.hFIX and BAD.I-SceI cassettes and the I-SceI site were eliminated, the ColE1 origin and the AmpR were replaced with the KanR, the FRT and attP sites and the plasmid replication origin R6K plus zeocin-resistance gene (Zeo) derived from the plasmid pCpG-mcs (InvivoGen). The plasmid pMC.ApoE.hFIX was made by stepwise replacement of the AmpR and the F1 origin in the plasmid pBS.8I-SceI with KanR and sApoE.hFIX and the flanking attB and attP sites from the plasmid p2φC31.hFIX$_6$, followed by the insertion of an additional 24 consecutive I-SceI recognition sites. The plasmid pMC.CM-V.LGNSO was made by replacing the attB.RSV.hAAT.attP fragment in the plasmid pMC.RSV.hAAT with the fragment flanked with the attB and attP derived from the plasmid p2φC31.LGNSO, as described previously. The plasmid placY.TetR was made by inserting the TetR sequence from pACYC184 (New England Biolabs) and flanked with PCR-generated 425 and 227 bp of the z and a lactose operon genes, respectively. Plasmid pbla.lacY A177C was made by inserting the beta-lactosidase gene promoter (bla) derived from pBlueScript fused with the lacY A177C cDNA derived from plasmid placY A177C. Plasmid p9attP.TetR.attB was made by replacing the z and a fragments in the plasmid placY.TetR with the attachment site (9attP) from bacteriophage TP901-1 and attB. Plasmid p4φC31.attP.9attB was generated by replacing the FRT and ZEO.R6K sequences of p2φC31.attP.FRT with the bacterial attachment site 9attB of bacteriophage TP901-1 and A101 from plasmid pBAD.Red$_{16}$, followed by insertion of two additional copies of the BAD.φC31 sequence.

Insertional inactivation of the endonuclease A gene in BW27783. This was achieved by Red-mediated homologous recombination between a linear DNA and the endA gene. To do this, BW27783 cells were transformed with pBAD.Red.

Cells from one transformed colony were used to make competent cells, as described. Briefly, the cells were cultured in 25 ml of low salt LB containing ampicillin (50 µg/ml) and 1% l-arabinose and incubated at 32° C. with shaking at 250 r.p.m. until the OD600 was 0.5. The competent cells were immediately transformed with 50 ng of the PmeI-restricted targeting DNA fragment prepared from pK$_a$nR.endA, cultured at 32° C. for 1 h, spread onto a plate containing kanamycin (Kan, 25 µg/ml) and incubated at 43° C. overnight. To select the KanR$_+$ colonies free of pBAD.Red, eight KanR$_+$ colonies were cultured in 500 µl LB with Kan at 43° C. for 30 min and 1 µl each was loaded onto the antibiotic-free, Kan$_+$, and Amp$_+$ plates, which were incubated at 43° C. overnight. To remove the KanR gene in the strain BWΔendA.KanR, competent cells were prepared from one KanR$_+$-colony, transformed with p2ϕC31 and spread onto a Amp$_+$ plate; subsequently, eight cultures were begun from eight p2ϕC31-transformed colonies in 500-µl antibiotic-free LB containing 1% l-arabinose at 32° C. for 2 h to induce the removal of KanR via ϕC31 integrase-mediated recombination between the attB and attP flanking the KanR, followed by 4 additional hours at 37° C. to induce I-SceI-mediated destruction of p2ϕC31. The cells were spread onto an antibiotic-free plate. Cells from eight colonies were cultured in 500 µl antibiotic-free LB at 37° C. for 30 min, and 1 µl each was loaded onto the antibiotic-free, Kan$_+$ and Amp$_+$ plates to select the AmpR_/KanR_ colonies. This resulted in the BWΔendA strain. The disruption of the endA gene was confirmed by DNA sequencing of the locus-specific PCR products generated from selected colonies.

Integration of the 2 l-arabinose transporter lacY A177C and three copies of the BAD.I-SceI gene. Replacement of the y gene (lacY) of the lactose operon with the mutant lacY A177C and integration of three copies of the I-SceI gene into the UMU locus were achieved by the same Red-mediated homology recombination protocol as described for the endA gene disruption. To integrate the lacY A177C, however, knockout of the wild-type lacY was performed before knocking in the lacY A177C. Both were accomplished using the same Red-mediated homologous recombination. We used a DNA fragment containing TetR flanked with fragments of the z and a genes to knock out lacY, and selected the intermediate, BWΔendA.TetR on the Tet$_+$ (6 µg/ml)-plate. This allowed the selection of the next integrant using differential KanR/TetR selection.

Integration of the BAD.ϕC31 cassettes. Three experiments were conducted to integrate ten copies of BAD.ϕC31 into the bacterial genome: two, four and four copies into the ΔendA locus, araD gene and galK gene, respectively. All three integration events were achieved by ϕC31 integrase-mediated, site-specific recombination between the attB or attP site in an integrating plasmid, and the attB or attP in the targeted genomic sites as described for the endA gene disruption.

In an earlier attempt, we found that the integrated BAD.ϕC31 was lost soon after its integration. This is probably the result of a reverse reaction mediated by an uncharacterized excisionase or cofactor that worked in concert with ϕC31 integrase produced by the leaky expression from the integrated BAD.ϕC31. To stabilize the integrant, we designed a double recombination strategy. The ϕC31 integrase was used to mediate an integration event followed by FLP- or TPin-mediated recombination to remove the attL. This would eliminate the possibility of a reverse reaction between the attL and attR. For integration of the 2BAD.ϕC31, we used the Red-mediated homologous recombination strategy with a linear DNA containing an attB site, a KanR gene and two flanking FRTs for insertion into the ΔendA locus. To remove the KanR, cells from one 3S2T.KanR colony were transformed with pcI587.FLP, and cells from a transformed colony were grown in 5 ml of antibiotic-free LB at 42° C. for 8 h. This induced the expression of FLP to mediate the recombination between the two FRTs, resulting in the elimination of KanR followed by the loss of the temperature-sensitive pcI587.FLP. Subsequently, the cells named 3S2T.attB were transformed with p2ϕC31.attP.FRT. Cells from one transformed colony were grown in 2-ml of LB containing 1% l-arabinose at 32° C. for 2 h, which induced the expression of ϕC31 integrase to mediate the recombination between the attB in the ΔendA locus and the attP in the plasmid. The same FLP-mediated FRT-FRT recombination was conducted to mediate the removal of the attL and R6K.Zeo and KanR, resulting in the strain of 2P3S2T. The integrated 2BAD.ϕC31 was confirmed by DNA sequencing of the locus-specific PCR product and by demonstrating the function in mediating minicircle formation. Integration of the four copies of the BAD.ϕC31 gene into the araD and galK loci, respectively, was also mediated by ϕC31 integrase; however, the removal of the attL was mediated by bacteriophage TP901-1 integrase (TPin). To do this, we used the Red recombination system to integrate a DNA fragment encoding TetR flanked with an attB and a phage attachment site of TPin (9attP) into the araD or galK site and confirmed the integrant by DNA sequencing of the integrant-specific PCR product. We integrated p4ϕC31.attP.9attB into the modified araD or galK locus following the same procedure as used for integrating the p2ϕC31.attP.FRT with modifications. We selected the colonies with integrants using plates containing both Tet and Kan, transformed the selected intermediates 6P3S2T.KanR.TetR or 10P3S2T.KanR.TetR with plasmid pBAD.TPin, and screened the resulting colonies using triple antibiotic resistance (Tet, Kan and Amp). We grew the cells from one colony in 2 ml of antibiotic-free LB containing 1% l-arabinose, with shaking (250 r.p.m.) at 43° C. for 6-8 h before spreading onto an antibiotic-free plate and incubated at 43° C. overnight. l-arabinose induced expression of both recombinases, however, the incubation temperature allowed significant TPin integrase activity but little ϕC31 integrase activity, resulting in the TPin integrase-mediated removal of attL and selection of colonies with the desired integrant, 6P3S2T and ZYCY10P3S2T.

Plasmid Glossary

1. P2øC31—a plasmid expresses øC31 integrase under the control of the L-arabinosearaC.BAD system; carrying a BAD.I-SceI cassette and an I-SceI site, the plasmid can be eliminated through overnight culture with 1% L-arabinose.

2. p2øC31.attP.FRT—a plasmid for integrating 2 copies of BAD.øC31 cassette through two FRT sites in the plasmid and in the genomic target, respectively; carrying the conditional R6K DNA origin and capable of replicating only in the cell expressing the pir protein, this plasmid will be cured in BW27783 and other common laboratory strain lacking the pir gene.

3. p2øC31.hFIX, an old version of minicircle producer plasmid encoding the ApoE.hFIX expression cassette, as described previously[2]. The makeup of the plasmid is shown as p2øC31.Transgene when the expression cassette is the ApoE.hFIX (ApoE HCR enhancer, hAAT promoter, hFIX minigene, and bovine poly A signal).

4. P2øC31.Transgene—the previous minicircle producer plasmid.

5. p3BAD.I-SceI—a plasmid for generating fragment DNA encoding 3 copies of BAD.ISceI cassette to be integrated through homologous recombination.

6. p4øC31.attP.9attP—a plasmid encoding 4 copies of BAD.øC31 cassette capable of integrating through the øC31 integrase-mediated recombination between the attP site in the plasmid and attB site in the genomic target.

7. p9attP.TetR.attB—a plasmid for integrating the TetR flanked with the attB and 9attP sites into the genomic target site; 9attP, the plasmid attachment site of the bacteriophage TP901-1 integrase (TPin).

8. pBAD.RED—a plasmid expressing the bacteriophage Lambda RED homologous recombinase system under the control of the L-arabinose-araC.BAD system; control under the heat sensitive DNA replication origin A101, it can be eliminated by growing the cells at 43° C. overnight.

9. pBAD.TPin—a plasmid expressing the TPin to mediate the elimination of unwanted or harmful DNA elements through recombination between 9attB and 9attP, under the control of the L-arabinose-araC.BAD system; similar to that of p2øC31, the plasmid carrying the BAD.I-SceI cassette and an I-SceI site, allowing its own degradation when inducing expression of I-SceI by L-arabinose.

10. pbla.LacY A177C—a plasmid for integrating the bla.LacY.A177C cassette at the disrupted LacY region. Bla, promoter of beta-lactosidase gene; A177C, an Alanine to Cysteine mutation at codon 177.

11. pBS.8I-SceIs—a pBlueScript base plasmid carrying 8 consecutive I-SceI sites.

12. pcI587.FLP—a plasmid expressing flipase, which mediates recombination between 2 FRT sites, under the control of bacteriophage Lambda pR promoter/cI587 repressor system.

13. pFRT.KanR.attB—a plasmid for generating PCR product encoding an attB site and the KanR flanked with 2 FRT sites up- and down-stream, respectively.

14. pKanR.endA—a plasmid for generating pme1-fragment to interrupt the endA gene.

15. pLacY.TetR—a plasmid for generating DNA fragment to disrupt the LacY locus with the selection marker, TetR.

16. pMC.ApoE.hFIX—a new version of minicircle producer plasmid for producing minicircle encoding the ApoE.hFIX expression cassette.

17. pMC.CMV.LGNSO—a new version of minicircle producing plasmid for production of the minicircle encoding the reporter gfp and a set of 4 transcription factors, including the LIN28, NANOG, SOX2 and OCT4, for converting somatic cells to iPS cells through reprogramming.

18. pMC.RSV.hAAT—a new version of minicircle producer plasmid for production of minicircle encoding the RSV.hAAT expression cassette (RSV-LTR promoter, hAAT cDNA, and bovine poly A signal).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for preparing a minicircle nucleic acid vector composition substantially free of contaminating nucleic acids, the method comprising:
    transfecting a genetically modified bacterial cell wherein the genetically modified bacterial cell genome comprises a disruption in an endA gene encoding endonuclease I and comprises a coding sequence for araE under control of a constitutive promoter, with a circular parental plasmid comprising:
    (i) a polynucleotide of interest flanked by attB and attP recombination sites recognized by a unidirectional site-specific recombinase;
    (ii) at least one restriction endonuclease site recognized by a restriction endonuclease not endogenous to the bacterial cell;
    wherein present in said circular parental plasmid or said bacterial cell are sequences encoding the unidirectional site-specific recombinase and the restriction endonuclease not endogenous to the bacterial cell;
    incubating the bacterial cells under conditions and for a period of time sufficient to express the unidirectional site-specific recombinase and allow the unidirectional site-specific recombinase to recombine the attB and attP recombination sites; and to express the restriction endonuclease and allow the restriction endonuclease to digest the restriction endonuclease site, wherein the incubating provides a minicircle nucleic acid vector comprising the polynucleotide of interest and a product hybrid sequence of the unidirectional site-specific recombinase;
    purifying the minicircle nucleic acid vector to provide a minicircle nucleic acid vector composition substantially free of contaminating nucleic acids comprising the nucleic acid coding sequence for the unidirectional site-specific recombinase and/or a restriction endonuclease.

2. The method of claim 1, wherein the polynucleotide of interest comprises an expression cassette.

3. The method of claim 1, wherein the minicircle nucleic acid vector is devoid of plasmid backbone bacterial DNA sequences.

4. The method of claim 1, wherein the unidirectional site-specific recombinase is under the control of a promoter inducible with L-arabinose.

5. The method of claim 1, wherein the restriction endonuclease not endogenous to the bacterial cell is under the control of a promoter inducible with L arabinose.

6. A method for integration of an exogenous genetic sequence in a genome of a targeted cell, the method comprising:
    introducing at a targeted site in a genome of a cell an attP or attB site;
    introducing into the cell a circular plasmid comprising the exogenous genetic sequence and the complementary attP or attB site wherein the exogenous genetic sequence is at least 10 kb in length;
    inducing expression of φC31 integrase in said cell, wherein the entire circular plasmid is integrated at the targeted site.

7. The method of claim 6, wherein the genome is a microbial genome.

8. The method of claim 7, wherein the genome is a bacterial genome.

9. The method of claim 6, wherein the exogenous genetic sequence is at least 20 kb.

10. The method of claim 6, further comprising the step of disabling the reverse excision reaction in the targeted cell with a second recombinase.

* * * * *